(12) United States Patent
DiPierro

(10) Patent No.: US 11,471,424 B2
(45) Date of Patent: *Oct. 18, 2022

(54) BIOSYNCHRONOUS TRANSDERMAL DRUG DELIVERY

(71) Applicant: Morningside Venture Investments Limited, Newton Centre, MA (US)

(72) Inventor: Guy DiPierro, San Francisco, CA (US)

(73) Assignee: Morningside Venture Investments Limited, Newton Centre, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/799,578

(22) Filed: Feb. 24, 2020

(65) Prior Publication Data

US 2020/0330369 A1 Oct. 22, 2020

Related U.S. Application Data

(63) Continuation of application No. 15/385,665, filed on Dec. 20, 2016, now abandoned, which is a
(Continued)

(51) Int. Cl.
*A61K 9/70* (2006.01)
*A61K 31/00* (2006.01)
(Continued)

(52) U.S. Cl.
CPC ............ *A61K 9/703* (2013.01); *A61K 9/0009* (2013.01); *A61K 9/0014* (2013.01); *A61K 31/00* (2013.01); *A61K 31/04* (2013.01); *A61K 31/137* (2013.01); *A61K 31/465* (2013.01); *A61M 37/00* (2013.01); *A61M 37/0015* (2013.01); *A61M 39/22* (2013.01); *A61M 37/0092* (2013.01); *A61M 2037/0007* (2013.01); *A61M 2037/0023* (2013.01); *A61M 2037/0061* (2013.01); *A61M 2205/0266* (2013.01);
(Continued)

(58) Field of Classification Search
None
See application file for complete search history.

(56) References Cited

U.S. PATENT DOCUMENTS 2,183,482 A 12/1939 Kurkjian
3,279,653 A 10/1966 Pfleger
(Continued)

FOREIGN PATENT DOCUMENTS

AU 662877 B 9/1995
BE 899037 A 6/1984
(Continued)

OTHER PUBLICATIONS

Abood et al.; Structure-activity studies of carbamate and other esters: agonists and antagonists to nicotine: Pharmacology Biochemistry and Behavior: 30(2); pp. 403-408; Jun. 1988.
(Continued)

*Primary Examiner* — Isis A Ghali
(74) *Attorney, Agent, or Firm* — Shay Glenn LLP

(57) ABSTRACT

Systems and methods for synchronizing the administration of compounds with the human body's natural circadian rhythms and addiction rhythms to counteract symptoms when they are likely to be at their worst by using an automated and preprogrammable transdermal or other drug administration system.

20 Claims, 5 Drawing Sheets

Related U.S. Application Data continuation of application No. 14/746,704, filed on Jun. 22, 2015, now Pat. No. 9,555,227, which is a continuation of application No. 14/162,156, filed on Jan. 23, 2014, now abandoned, which is a continuation of application No. 11/162,517, filed on Sep. 13, 2005, now abandoned.

(60) Provisional application No. 60/609,418, filed on Sep. 13, 2004.

(51) Int. Cl.
| | | |
|---|---|---|
| *A61K 9/00* | (2006.01) | |
| *A61M 37/00* | (2006.01) | |
| *A61K 31/04* | (2006.01) | |
| *A61K 31/137* | (2006.01) | |
| *A61K 31/465* | (2006.01) | |
| *A61M 39/22* | (2006.01) | |
| *A61N 1/30* | (2006.01) | |

(52) U.S. Cl.
CPC . *A61M 2205/3337* (2013.01); *A61M 2205/50* (2013.01); *A61N 1/30* (2013.01)

(56) References Cited

U.S. PATENT DOCUMENTS

| | | |
|---|---|---|
| 3,845,217 A | 10/1974 | Ferno et al. |
| 4,313,439 A | 2/1982 | Babb et al. |
| 4,321,387 A | 3/1982 | Chavdarian et al. |
| 4,327,725 A | 5/1982 | Cortese et al. |
| 4,332,945 A | 6/1982 | Edwards |
| 4,379,454 A | 4/1983 | Campbell et al. |
| 4,545,990 A | 10/1985 | Le Foyer de Costil et al. |
| 4,579,858 A | 4/1986 | Ferno et al. |
| 4,590,278 A | 5/1986 | Edwards |
| 4,708,716 A | 11/1987 | Sibalis |
| 4,772,263 A | 9/1988 | Dorman et al. |
| 4,806,356 A | 2/1989 | Shaw |
| 4,853,854 A | 8/1989 | Behar et al. |
| 4,885,154 A | 12/1989 | Cormier et al. |
| 4,908,213 A | 3/1990 | Govil et al. |
| 4,917,676 A | 4/1990 | Heiber et al. |
| 4,917,895 A | 4/1990 | Lee et al. |
| 4,920,989 A | 5/1990 | Rose et al. |
| 4,952,928 A | 8/1990 | Carroll et al. |
| 4,953,572 A | 9/1990 | Rose et al. |
| 4,992,445 A | 2/1991 | Lawter et al. |
| 5,000,956 A | 3/1991 | Amkraut et al. |
| 5,001,139 A | 3/1991 | Lawter et al. |
| 5,013,293 A | 5/1991 | Sibalis |
| 5,023,252 A | 6/1991 | Hseih |
| 5,049,387 A | 9/1991 | Amkraut |
| 5,069,904 A | 12/1991 | Masterson |
| 5,073,380 A | 12/1991 | Babu et al. |
| 5,097,834 A | 3/1992 | Skrabal |
| 5,120,545 A | 6/1992 | Ledger et al. |
| 5,130,139 A | 7/1992 | Cormier et al. |
| 5,149,538 A | 9/1992 | Granger et al. |
| 5,149,719 A | 9/1992 | Ferber et al. |
| 5,212,188 A | 5/1993 | Caldwell et al. |
| 5,221,254 A | 6/1993 | Phipps |
| 5,227,391 A | 7/1993 | Caldwell et al. |
| 5,232,704 A | 8/1993 | Franz et al. |
| 5,232,933 A | 8/1993 | Lippiello et al. |
| 5,236,714 A | 8/1993 | Lee et al. |
| 5,242,934 A | 9/1993 | Lippiello et al. |
| 5,242,935 A | 9/1993 | Lippiello et al. |
| 5,242,941 A | 9/1993 | Lewy et al. |
| 5,248,690 A | 9/1993 | Caldwel et al. |
| 5,252,604 A | 10/1993 | Nagy et al. |
| 5,262,165 A | 11/1993 | Govil et al. |
| 5,273,755 A | 12/1993 | Venkatraman et al. |
| 5,273,756 A | 12/1993 | Fallon et al. |
| 5,304,739 A | 4/1994 | Klug et al. |
| 5,310,404 A | 5/1994 | Gyory et al. |
| 5,352,456 A | 10/1994 | Fallon et al. |
| 5,364,630 A | 11/1994 | Osborne et al. |
| 5,370,635 A | 12/1994 | Strausak et al. |
| 5,388,571 A | 2/1995 | Roberts et al. |
| 5,389,679 A | 2/1995 | Alliger |
| 5,393,526 A | 2/1995 | Castro |
| 5,405,614 A | 4/1995 | D'Angelo et al. |
| 5,415,629 A | 5/1995 | Henley |
| 5,445,609 A | 8/1995 | Lattin et al. |
| 5,451,407 A | 9/1995 | Cormier et al. |
| 5,464,387 A | 11/1995 | Haak et al. |
| 5,472,946 A | 12/1995 | Peck et al. |
| 5,501,697 A | 3/1996 | Fisher |
| 5,505,958 A | 4/1996 | Bello et al. |
| 5,512,306 A | 4/1996 | Carlsson et al. |
| 5,516,793 A | 5/1996 | Duffy |
| 5,525,351 A | 6/1996 | Dam |
| 5,545,407 A | 8/1996 | Hall et al. |
| 5,562,607 A | 10/1996 | Gyory |
| 5,596,994 A | 1/1997 | Bro |
| 5,601,839 A | 2/1997 | Quan et al. |
| 5,616,332 A | 4/1997 | Herstein |
| 5,618,557 A | 4/1997 | Wille et al. |
| 5,653,682 A | 8/1997 | Sibalis |
| 5,656,255 A | 8/1997 | Jones |
| 5,662,920 A | 9/1997 | Santus |
| 5,686,100 A | 11/1997 | Wille et al. |
| 5,688,232 A | 11/1997 | Flower |
| 5,697,896 A | 12/1997 | McNichols et al. |
| 5,716,987 A | 2/1998 | Wille |
| 5,722,418 A | 3/1998 | Bro |
| 5,733,259 A | 3/1998 | Valcke et al. |
| 5,785,688 A | 7/1998 | Joshi et al. |
| 5,797,867 A | 8/1998 | Guerrera et al. |
| 5,820,875 A | 10/1998 | Fallon et al. |
| 5,833,466 A | 11/1998 | Borg |
| 5,843,979 A | 12/1998 | Wille et al. |
| 5,846,559 A | 12/1998 | Hopp |
| 5,865,786 A | 2/1999 | Sibalis et al. |
| 5,876,368 A | 3/1999 | Flower |
| 5,879,292 A | 3/1999 | Sternberg et al. |
| 5,879,322 A | 3/1999 | Lattin et al. |
| 5,882,676 A | 3/1999 | Lee et al. |
| 5,908,301 A | 6/1999 | Lutz |
| 5,919,156 A | 7/1999 | Stropkay et al. |
| 5,932,240 A | 8/1999 | D'Angelo et al. |
| 5,945,123 A | 8/1999 | Hermelin |
| 5,967,789 A | 10/1999 | Segel et al. |
| 5,972,389 A | 10/1999 | Shell et al. |
| 5,993,435 A | 11/1999 | Haak et al. |
| 5,997,501 A | 12/1999 | Gross et al. |
| 6,018,679 A | 1/2000 | Dinh et al. |
| 6,019,997 A | 2/2000 | Scholz et al. |
| 6,024,981 A | 2/2000 | Khankari et al. |
| 6,034,079 A | 3/2000 | Sanberg et al. |
| 6,059,736 A | 5/2000 | Tapper |
| 6,059,753 A | 5/2000 | Faust et al. |
| 6,068,853 A | 5/2000 | Giannos et al. |
| 6,081,734 A | 6/2000 | Batz |
| 6,090,404 A | 7/2000 | Meconi et al. |
| 6,093,419 A | 7/2000 | Rolf |
| 6,120,803 A | 9/2000 | Wong et al. |
| 6,129,702 A | 10/2000 | Woias et al. |
| 6,162,214 A | 12/2000 | Mueller et al. |
| 6,165,155 A | 12/2000 | Jacobsen et al. |
| 6,211,194 B1 | 4/2001 | Westman et al. |
| 6,211,296 B1 | 4/2001 | Frate et al. |
| 6,221,394 B1 | 4/2001 | Gilbert et al. |
| 6,238,689 B1 | 5/2001 | Rhodes et al. |
| 6,274,606 B1 | 8/2001 | Caldwell et al. |
| 6,310,102 B1 | 10/2001 | Dull et al. |
| 6,365,182 B1 | 4/2002 | Khankari et al. |
| 6,368,625 B1 | 4/2002 | Siebert et al. |
| 6,374,136 B1 | 4/2002 | Murdock |
| 6,416,471 B1 | 7/2002 | Kumar et al. |
| 6,417,359 B1 | 7/2002 | Crooks et al. |
| 6,423,747 B1 | 7/2002 | Lanzendörfer et al. |

(56) References Cited

U.S. PATENT DOCUMENTS

| | | |
|---|---|---|
| 6,436,078 B1 | 8/2002 | Svedman |
| 6,437,004 B1 | 8/2002 | Perricone |
| 6,454,708 B1 | 9/2002 | Ferguson et al. |
| 6,488,959 B2 | 12/2002 | Stanley et al. |
| 6,492,399 B1 | 12/2002 | Dull et al. |
| 6,539,250 B1 | 3/2003 | Bettinger |
| 6,546,281 B1 | 4/2003 | Zhang et al. |
| 6,567,785 B2 | 5/2003 | Clendenon |
| 6,569,449 B1 | 5/2003 | Stinchcomb et al. |
| 6,569,866 B2 | 5/2003 | Simon |
| 6,576,269 B1 | 6/2003 | Korneyev |
| 6,579,865 B2 | 6/2003 | Mak et al. |
| 6,589,229 B1 | 7/2003 | Connelly et al. |
| 6,595,956 B1 | 7/2003 | Gross et al. |
| 6,638,528 B1 | 10/2003 | Kanios |
| 6,638,543 B2 | 10/2003 | Kang et al. |
| 6,660,295 B2 | 12/2003 | Watanabe et al. |
| 6,689,380 B1 | 2/2004 | Marchitto et al. |
| 6,723,086 B2 | 4/2004 | Bassuk et al. |
| 6,723,340 B2 | 4/2004 | Gusler et al. |
| 6,746,688 B1 | 6/2004 | Kushnir et al. |
| 6,791,003 B1 | 9/2004 | Choi et al. |
| 6,799,576 B2 | 10/2004 | Farr |
| 6,849,645 B2 | 2/2005 | Majeed et al. |
| 6,861,066 B2 | 3/2005 | Van de Casteele |
| 6,867,342 B2 | 3/2005 | Johnston et al. |
| 6,887,202 B2 | 5/2005 | Currie et al. |
| 6,893,655 B2 | 5/2005 | Flanigan et al. |
| 6,900,202 B2 | 5/2005 | Imoto et al. |
| 6,911,475 B1 | 6/2005 | Villafane et al. |
| 6,998,176 B2 | 2/2006 | Morita et al. |
| 7,011,843 B2 | 3/2006 | Becher et al. |
| 7,011,849 B2 | 3/2006 | Storm et al. |
| 7,019,622 B2 | 3/2006 | Orr et al. |
| 7,064,143 B1 | 6/2006 | Gurley et al. |
| 7,182,955 B2 | 2/2007 | Hart et al. |
| 7,196,619 B2 | 3/2007 | Perlman et al. |
| 7,229,641 B2 | 6/2007 | Cherukuri |
| 7,282,217 B1 | 10/2007 | Grimshaw et al. |
| 7,332,182 B2 | 2/2008 | Sackler |
| 7,376,700 B1 | 5/2008 | Clark et al. |
| 7,384,651 B2 | 6/2008 | Hille et al. |
| 7,384,653 B2 | 6/2008 | Wright et al. |
| 7,579,019 B2 | 8/2009 | Tapolsky et al. |
| 7,598,275 B2 | 10/2009 | Cooke et al. |
| 7,718,677 B2 | 5/2010 | Quik et al. |
| 7,780,981 B2 | 8/2010 | DiPierro et al. |
| 7,988,660 B2 | 8/2011 | Byland et al. |
| 8,003,080 B2 | 8/2011 | Rabinowitz et al. |
| 8,021,334 B2 | 9/2011 | Shekalim |
| 8,192,756 B2 | 6/2012 | Berner et al. |
| 8,252,321 B2 | 8/2012 | DiPierro et al. |
| 8,262,394 B2 | 9/2012 | Walker et al. |
| 8,268,475 B2 | 9/2012 | Tucholski |
| 8,372,040 B2 | 2/2013 | Huang et al. |
| 8,440,220 B2 | 5/2013 | Gale et al. |
| 8,440,221 B2 | 5/2013 | Zumbrunn et al. |
| 8,445,010 B2 | 5/2013 | Anderson et al. |
| 8,574,188 B2 | 11/2013 | Potter et al. |
| 8,586,079 B2 | 11/2013 | Hansted et al. |
| 8,589,174 B2 | 11/2013 | Nelson et al. |
| 8,673,346 B2 | 3/2014 | Zumbrunn et al. |
| 8,688,189 B2 | 4/2014 | Shennib |
| 8,690,827 B2 | 4/2014 | Edwards et al. |
| 8,690,865 B2 | 4/2014 | Prausnitz et al. |
| 8,703,175 B2 | 4/2014 | Kanios et al. |
| 8,722,233 B2 | 5/2014 | Tucholski |
| 8,727,745 B2 | 5/2014 | Rush et al. |
| 8,741,336 B2 | 6/2014 | DiPierro et al. |
| 8,865,207 B2 | 10/2014 | Kanios et al. |
| 8,999,356 B1 | 4/2015 | Ramirez et al. |
| 8,999,372 B2 | 4/2015 | Davidson et al. |
| 9,023,392 B2 | 5/2015 | Koo et al. |
| 9,078,833 B2 | 7/2015 | Audett |
| 9,155,712 B2 | 10/2015 | Kanios et al. |
| 9,233,203 B2 | 1/2016 | Moberg et al. |
| 9,238,108 B2 | 1/2016 | Edwards et al. |
| 9,289,397 B2 | 3/2016 | Wright |
| RE46,217 E | 11/2016 | Huang et al. |
| 9,555,226 B2 | 1/2017 | Zumbrunn et al. |
| 9,555,227 B2 | 1/2017 | Dipierro |
| 9,669,199 B2 | 6/2017 | DiPierro et al. |
| 9,687,186 B2 | 6/2017 | Goldstein et al. |
| 9,795,681 B2 | 10/2017 | Abreu |
| 10,034,841 B2 | 7/2018 | Müller et al. |
| 10,105,487 B2 | 10/2018 | DiPierro et al. |
| 10,213,586 B2 | 2/2019 | Netzel et al. |
| 10,232,156 B2 | 3/2019 | Netzel et al. |
| 10,258,738 B2 | 4/2019 | Dipierro et al. |
| 10,258,778 B2 | 4/2019 | DiPierro et al. |
| 10,679,516 B2 | 6/2020 | Darmour et al. |
| 10,716,764 B2 | 7/2020 | Zumbrunn et al. |
| 2001/0022978 A1 | 9/2001 | Lacharriere et al. |
| 2001/0026788 A1 | 10/2001 | Piskorz |
| 2002/0002189 A1 | 1/2002 | Smith et al. |
| 2002/0034535 A1 | 3/2002 | Kleiner et al. |
| 2002/0106329 A1 | 8/2002 | Leslie |
| 2002/0127256 A1 | 9/2002 | Murad |
| 2002/0165170 A1 | 11/2002 | Wilson et al. |
| 2002/0169439 A1 | 11/2002 | Flaherty |
| 2002/0182238 A1 | 12/2002 | Cretan |
| 2003/0004187 A1 | 1/2003 | Bedard et al. |
| 2003/0065294 A1 | 4/2003 | Pickup et al. |
| 2003/0065924 A1 | 4/2003 | Wuidart et al. |
| 2003/0083645 A1 | 5/2003 | Angel et al. |
| 2003/0087937 A1 | 5/2003 | Lindberg |
| 2003/0119879 A1 | 6/2003 | Landh et al. |
| 2003/0159702 A1 | 8/2003 | Lindell et al. |
| 2004/0019321 A1 | 1/2004 | Sage et al. |
| 2004/0034068 A1 | 2/2004 | Warchol et al. |
| 2004/0037879 A1 | 2/2004 | Adusumilli et al. |
| 2004/0052843 A1 | 3/2004 | Lerner et al. |
| 2004/0062802 A1 | 4/2004 | Hermelin |
| 2004/0138074 A1 | 7/2004 | Ahmad et al. |
| 2004/0166159 A1 | 8/2004 | Han et al. |
| 2004/0191322 A1 | 9/2004 | Hansson |
| 2004/0194793 A1 | 10/2004 | Lindell et al. |
| 2004/0219192 A1 | 11/2004 | Horstmann et al. |
| 2004/0229908 A1 | 11/2004 | Nelson |
| 2004/0241218 A1 | 12/2004 | Tavares et al. |
| 2004/0253249 A1 | 12/2004 | Rudnic et al. |
| 2004/0259816 A1 | 12/2004 | Pandol et al. |
| 2005/0002806 A1 | 1/2005 | Fuechslin et al. |
| 2005/0014779 A1 | 1/2005 | Papke |
| 2005/0021092 A1 | 1/2005 | Yun et al. |
| 2005/0034842 A1 | 2/2005 | Huber et al. |
| 2005/0048020 A1 | 3/2005 | Wille |
| 2005/0053665 A1 | 3/2005 | Ek et al. |
| 2005/0113452 A1 | 5/2005 | Flashner Barak et al. |
| 2005/0141346 A1 | 6/2005 | Rawls et al. |
| 2005/0151110 A1 | 7/2005 | Minor et al. |
| 2005/0159419 A1 | 7/2005 | Stephenson et al. |
| 2005/0197625 A1 | 9/2005 | Haueter et al. |
| 2005/0266032 A1 | 12/2005 | Srinivasan et al. |
| 2005/0276852 A1 | 12/2005 | Davis et al. |
| 2006/0024358 A1 | 2/2006 | Santini et al. |
| 2006/0036209 A1 | 2/2006 | Subramony et al. |
| 2006/0057202 A1 | 3/2006 | Antarkar et al. |
| 2006/0122577 A1 | 6/2006 | Poulsen et al. |
| 2006/0135911 A1 | 6/2006 | Mittur |
| 2006/0167039 A1 | 7/2006 | Nguyen et al. |
| 2006/0184093 A1 | 8/2006 | Phipps et al. |
| 2006/0188859 A1 | 8/2006 | Yakobi |
| 2006/0204578 A1 | 9/2006 | Vergez et al. |
| 2006/0206054 A1 | 9/2006 | Shekalim |
| 2007/0026054 A1 | 2/2007 | Theobald et al. |
| 2007/0042026 A1 | 2/2007 | Wille |
| 2007/0065365 A1 | 3/2007 | Kugelmann et al. |
| 2007/0086275 A1 | 4/2007 | Robinson et al. |
| 2007/0088338 A1 | 4/2007 | Ehwald et al. |
| 2007/0149952 A1 | 6/2007 | Bland et al. |
| 2007/0154336 A1 | 7/2007 | Miyazaki et al. |
| 2007/0168501 A1 | 7/2007 | Cobb et al. |
| 2007/0179172 A1 | 8/2007 | Becker et al. |

(56) References Cited

U.S. PATENT DOCUMENTS

| | | |
|---|---|---|
| 2007/0191815 A1 | 8/2007 | DiPierro |
| 2007/0250018 A1 | 10/2007 | Adachi et al. |
| 2008/0138294 A1 | 6/2008 | Gonda |
| 2008/0138398 A1 | 6/2008 | Gonda |
| 2008/0138399 A1 | 6/2008 | Gonda |
| 2008/0138423 A1 | 6/2008 | Gonda |
| 2008/0139907 A1 | 6/2008 | Rao et al. |
| 2008/0201174 A1 | 8/2008 | Ramasubramanian et al. |
| 2008/0233178 A1 | 9/2008 | Reidenberg et al. |
| 2008/0274168 A1 | 11/2008 | Baker et al. |
| 2009/0024004 A1 | 1/2009 | Yang |
| 2009/0118710 A1 | 5/2009 | Kortzeborn |
| 2010/0068250 A1 | 3/2010 | Anderson et al. |
| 2010/0114008 A1 | 5/2010 | Marchitto et al. |
| 2010/0196463 A1 | 8/2010 | Quik et al. |
| 2010/0280432 A1 | 11/2010 | DiPierro et al. |
| 2011/0137255 A1 | 6/2011 | Nielsen et al. |
| 2013/0017259 A1 | 1/2013 | Azhir |
| 2013/0158430 A1 | 6/2013 | Aceti et al. |
| 2014/0073883 A1 | 3/2014 | Rao et al. |
| 2014/0200525 A1 | 7/2014 | DiPierro |
| 2014/0207047 A1 | 7/2014 | DiPierro et al. |
| 2014/0228736 A1 | 8/2014 | Eppstein et al. |
| 2016/0220553 A1 | 8/2016 | Azhir |
| 2016/0235732 A1 | 8/2016 | Quik et al. |
| 2016/0235916 A1 | 8/2016 | Edwards et al. |
| 2017/0100573 A1 | 4/2017 | DiPierro |
| 2018/0110768 A1 | 4/2018 | Quik et al. |
| 2018/0374381 A1 | 12/2018 | Darmour et al. |
| 2019/0054078 A1 | 2/2019 | Azhir et al. |
| 2019/0054235 A1 | 2/2019 | DiPierro et al. |
| 2019/0231707 A1 | 8/2019 | Stiles et al. |
| 2019/0275308 A1 | 9/2019 | Netzel et al. |
| 2019/0336738 A1 | 11/2019 | Johnson et al. |
| 2019/0374482 A1 | 12/2019 | Schaller et al. |
| 2020/0030590 A1 | 1/2020 | Buchman et al. |
| 2021/1096935 | 7/2021 | Tong et al. |

FOREIGN PATENT DOCUMENTS

| | | | |
|---|---|---|---|
| CA | 2142871 A1 | 3/1994 |
| CN | 1704056 A | 12/2005 |
| DE | 19958554 A1 | 1/2001 |
| DE | 10105759 C1 | 10/2001 |
| DE | 10103158 A1 | 8/2002 |
| EP | 311313 A2 | 4/1989 |
| EP | 0314528 B1 | 12/1992 |
| EP | 0354554 B1 | 1/1994 |
| EP | 0726005 A1 | 8/1996 |
| EP | 857725 A1 | 8/1998 |
| EP | 870768 A1 | 10/1998 |
| EP | 955301 A2 | 11/1999 |
| EP | 0612525 B1 | 9/2001 |
| EP | 1662989 B1 | 9/2014 |
| GB | 1528391 A | 10/1978 |
| GB | 2030862 A | 4/1980 |
| GB | 2142822 A | 1/1985 |
| GB | 2230439 A | 10/1990 |
| JP | 02202813 A | 8/1990 |
| JP | H09504974 A | 5/1997 |
| JP | 09512006 A | 12/1997 |
| JP | 2000515394 A | 11/2000 |
| JP | 2001505491 A | 4/2001 |
| JP | 2002092180 A | 3/2002 |
| JP | 2003506477 A | 2/2003 |
| JP | 2005521526 A | 7/2005 |
| JP | 2005525147 A | 8/2005 |
| JP | 2010279808 A | 12/2010 |
| WO | WO86/07269 A1 | 12/1986 |
| WO | WO88/003803 A1 | 6/1988 |
| WO | WO91/14441 A1 | 10/1991 |
| WO | WO92/021339 A1 | 12/1992 |
| WO | WO94/008992 A1 | 4/1994 |
| WO | WO94/010987 A1 | 5/1994 |
| WO | WO95/06497 A1 | 3/1995 |
| WO | WO96/015123 A1 | 5/1996 |
| WO | WO96/040682 A1 | 12/1996 |
| WO | WO97/011072 A1 | 3/1997 |
| WO | WO97/011073 A1 | 3/1997 |
| WO | WO97/11741 A1 | 4/1997 |
| WO | WO97/18782 A1 | 5/1997 |
| WO | WO97/019059 A1 | 5/1997 |
| WO | WO97/028801 A1 | 8/1997 |
| WO | WO97/034605 A1 | 9/1997 |
| WO | WO97/042941 A2 | 11/1997 |
| WO | WO97/046554 A1 | 12/1997 |
| WO | WO98/042713 A1 | 10/1998 |
| WO | WO98/46093 A1 | 10/1998 |
| WO | WO98/054152 A1 | 12/1998 |
| WO | WO98/054181 A1 | 12/1998 |
| WO | WO98/054182 A1 | 12/1998 |
| WO | WO98/054189 A1 | 12/1998 |
| WO | WO98/55107 A1 | 12/1998 |
| WO | WO99/002517 A1 | 1/1999 |
| WO | WO99/003859 A1 | 1/1999 |
| WO | WO99/021834 A1 | 5/1999 |
| WO | WO99/024422 A1 | 5/1999 |
| WO | WO99/066916 A1 | 12/1999 |
| WO | WO00/010997 A1 | 3/2000 |
| WO | WO00/032600 A1 | 6/2000 |
| WO | WO00/034279 A1 | 6/2000 |
| WO | WO00/034284 A1 | 6/2000 |
| WO | WO00/035279 A1 | 6/2000 |
| WO | WO00/035456 A1 | 6/2000 |
| WO | WO00/044755 A1 | 8/2000 |
| WO | WO00/064885 A1 | 11/2000 |
| WO | WO00/066596 A1 | 11/2000 |
| WO | WO00/74763 A2 | 12/2000 |
| WO | WO00/74933 A1 | 12/2000 |
| WO | WO01/005459 A1 | 1/2001 |
| WO | WO01/037814 A1 | 5/2001 |
| WO | WO02/076211 A1 | 10/2002 |
| WO | WO03/022349 A2 | 3/2003 |
| WO | WO03/026655 A1 | 4/2003 |
| WO | WO03/055486 A1 | 7/2003 |
| WO | WO03/061656 A1 | 7/2003 |
| WO | WO03/070191 A1 | 8/2003 |
| WO | WO03/097146 A1 | 11/2003 |
| WO | WO2004/024124 A1 | 3/2004 |
| WO | WO2004/073429 A1 | 9/2004 |
| WO | WO2005/023227 A2 | 3/2005 |
| WO | WO2005/079161 A2 | 9/2005 |
| WO | WO2006/069097 A2 | 6/2006 |
| WO | WO2007/013975 A2 | 2/2007 |
| WO | WO2008/069970 A2 | 6/2008 |
| WO | WO2008/069972 A2 | 6/2008 |

OTHER PUBLICATIONS

Ahlskog et al.; Frequency of levodopa-related dyskinesias and motor fluctuations as estimated from the cumulative literature; Movement Disorders; 16(3); pp. 448-458; May 1, 2001.

Angulo et al.; Oral nicotine in treatment of primary sclerosing cholangitis: a pilot study; Digestive diseases and sciences; 44(3); pp. 602-607; Mar. 1, 1999.

Baldessarini et al.: Preclinical studies of the pharmacology of aporphines; In: Gessa GL, Corsini GU, eds.; Apomorphine and other dopaminomi-'metics vol. 1, Basic pharmacology; New York: Raven Press; pp. 219-228; (year of pub. sufficiently earlier than effective US filing date and any foreign priority date) 1981.

Balfour et al.; Pharmacology of nicotine and its therapeutic use in smoking cessation and neurodegenerative disorders; Pharmacology and Therapeutics; 72(1); pp. 51-81; Jan. 1, 1996.

Benowitz et al.; Sources of variability in nicotine and cotinine levels with use of nicotine nasal spray, transdermal nicotine, and cigarette smoking, British Journal of Clinical Pharmacology; 43(3); pp. 259-267; Mar. 1, 1997.

Benowitz et al.; Stable isotope studies of nicotine kinetics and bioavailability; Clin Pharm and Ther; 49(3); pp. 270-277; Mar. 1991.

Bove et al.; Toxin-induced models of Parkinson's disease; NeuroRx; 2(3); pp. 484-494; Jul. 31, 2005.

(56) References Cited

OTHER PUBLICATIONS

Brotchie et al.; Levodopa-induced dyskinesia in Parkinson's disease; Journal of Neural Transmission; 112(3); pp. 359-391; Mar. 1, 2005.
Bruguerolle; Chronopharmacokinetics; Clin Pharmacokinet; 35(2); pp. 83-94; Aug. 1998.
Chen et al.; Enhanced striatal opioid receptor-mediated G-protein activation in L-DOPA-treated dyskinetic monkeys; Neuroscience; 132(2); pp. 409-420; Dec. 31, 2005.
Damaj et al.; Antinociceptive responses to nicotinic acetylcholine receptor ligands after systemic and intrathecal administration in mice; Journal of Pharmacology and Experimental Therapeutics; 284(3); pp. 1058-1065; Mar. 1, 1998.
De La Fuente et al.; The placebo effect in Parkinson's disease; Trends in Neuroscience; 25(6); pp. 302-306; Jun. 1, 2002.
Di Monte et al.; Relationship among nigrostriatal denervation, parkinsonism, and dyskinesias in the MPTP primate model; Movement Disorders; 15(3); pp. 459-466; May 1, 2000.
Dockser-Marcus, A.; New research shows drugs work best at certain times; The Wall Street Journal; 6 pgs.; May 27, 2003; (http://www.wsj.com/articles/SB105397312486508700).
Domino et al.; Nicotine alone and in combination with L-DOPA methyl ester or the D(2) agonist N-0923 in MPTP-induced chronic hemiparkinsonian monkeys; Exp Neurol; 158(2); pp. 414-421; Aug. 1999.
Ebersbach et al.; Worsening of motor performance in patients with Parkinson's disease following transdermal nicotine administration; Movement Disorders; 14(6); pp. 1011-1013; Nov. 1, 1999.
Ethicon Endo-Surgery, Inc.; Sedasys® Computer-assisted personalized sedation system essential product information; retrieved May 12, 2015 from the internet (http://www.sedasys.com/explore-the-system/essential-product-information); 2 pgs.
Fagerstrom et al.; Nicotine may relieve symptoms of Parkinson's disease; Psychopharmacology; 116(1); pp. 117-119; Sep. 16, 1994.
Food and Drug Administration; Guidance for Industry—Dissolution Testing of Immediate Release Solid Oral Dosage Forms; 17 pages; retrieved from the internet (https://www.fda.gov/downloads/drugs/guidances/ucm070237.pdf); Aug. 1997.
Gatto et al.; TC-1734: An orally active neuronal nicotinic acetylcholine receptor modulator with antidepressant, neuroprotective and long-lasting cognitive effects; CNS Drug Reviews; 10(2); pp. 147-166; Jun. 1, 2004.
Gennaro (Editor); Remington: The Science and Practice of Pharmacy; 19th Ed.; Mack Publishing Co.; Easton, PA; p. 1582-1584; Jun. 1995.
Gora; Nicotine transdermal systems; The Annals of Pharmacotherapy; 27(6); pp. 742-750; Jun. 1993.
Green et al.; An oral formulation of nicotine for release and absorption in the colon: its development and pharmacokinetics. British Journal of Clinical Pharmacology; 48(4); pp. 485-493; Oct. 1999.
Gries et al.; Importance of Chronopharmacokinetics in Design and Evaluation of Transdermal Drug Delivery Systems; J Pharmacol Exp Ther; 285(2); pp. 457-463; May 1998.
Guy; Current status and future prospects of transdermal drug delivery; Pharm Res; 13(12); pp. 1765-1769; Dec. 1996.
Halberg et al.; Chronomics: circadian and circaseptan timing of radiotherapy, drugs, calories, perhaps nutriceuticals and beyond; Journal of Experimental Therapeutics and Oncology; 3(5); pp. 223-260; Sep. 2003.
He et al.; Autoradiographic analysis of dopamine receptor-stimulated [35S]GTPtS binding in rat striatum; Brain Research; 885(1); pp. 133-136; Dec. 1, 2000.
He et al; Autoradiographic analysis of N-methyl-D-aspartate receptor binding in monkey brain: Effects of I-methyl-4-phenyl-1,2,3,6-tetrahydropyridine andlevodopa treatment; Neuroscience; 99(4); pp. 697-704; Aug. 23, 2000.
Hrushesky; Temporally optimizable delivery systems: sine qua non for the next therapeutic revolution; J Cont Rel; 19(1-3); pp. 363-368; Mar. 1992.

Hsu et al.; Effect of the D3 dopamine receptor partial agonist BP897 [N-[4-(4-(2-methoxyphenyl)piperazinyl) butyl]-2-napthamide] on L-3,4-dihydroxyphenylalanine-induced dyskinesias and parkinsonism in squirrel monkeys; The Journal of Pharmacology and Experimental Therapeutics. 311(2): pp. 770-777; Nov. 1, 2004.
Huang et al.; Inhibitory effects of curcumin on in vitro lipoxygenase and cyclooxygenase activities in mouse epidermis; Cancer Res; 51(3); pp. 813-819; Feb. 1991.
Hukkanen et al.; Metabolism and disposition kinetics of nicotine; Pharmacological Reviews; 57(1); pp. 79-115; Mar. 1, 2005.
Ingram et al.; Preliminary observations of oral nicotine therapy for inflammatory bowel disease: an open-label phase I-II study of tolerance; Inflamm Bowel Diseases; 11(12); pp. 1092-1096; Dec. 1, 2005.
Janson et al.; Chronic nicotine treatment counteracts dopamine D2 receptor upregulation induced by a partial meso-diencephalic hemitransection in the rat; Brain Res.; 655(1-2); pp. 25-32; Aug. 29, 1994.
Jarvik et al.; Inhibition of cigarette smoking by orally administered nicotine; Clinical Pharmacology and Therapeutics; 11(4); pp. 574-576; Jul. 1, 1970.
Jeyarasasingam et al.; Nitric oxide is involved in acetylcholinesterase inhibitor-induced myopathy in rats; The Journal of Pharmacology and Experimental Therapeutics; 295(1); pp. 314-320; Oct. 1, 2000.
Jeyarasasingam et al.,; Stimulation of non-o7 nicotinic receptors partially protects dopaminergic neurons from 1-methyl-4-phenylpyridinium-induced toxicity in culture; Neuroscience; 109(2); pp. 275-285; Jan. 28, 2002.
Jeyarasasingam et al.; Tacrine, a reversible acetylcholinesterase inhibitor, induces myopathy; Neuroreport; 11(6); pp. 1173-1176; Apr. 27, 2000.
Kalish et al.; Prevention of contact hypersensitivity to topically applied drugs by ethacrynic acid: potential application to transdermal drug delivery; J. Controll Rel; 48(1); pp. 79-87; Sep. 1997.
Kalish et al.; Sensitization of mice to topically applied drugs: albuterol, chlorpheniramine, clonidine and nadolol; Contact Dermatitis; 35(2); pp. 76-82; Aug. 1996.
Kelton et al.; The effects of nicotine on Parkinson's disease; Brain Cognition; 43(1-3); pp. 274-282; Jun. 2000.
Kiwi Drug; Buy nicorette microtabs; 3 pages; retrieved from the internet (www.kiwidrug.com/search/nicorette_microtabs); on Jul. 26, 2018.
Kulak et al.; 5-lodo-A-85380 binds to oconotoxin Mil-sensitive nicotinic acetylcholine receptors (nAChRs) as well as o4j32* subtypes; Journal of Neurochemistry; 81 (2); pp. 403-406; Apr. 1, 2002.
Kulak et al.; Declines in different pi* nicotinic receptor populations in monkey striatum after nigrostriatal damage; The Journal of Pharmacology and Experimental Therapeutics; 303(2); pp. 633-639; Nov. 1, 2002.
Kulak et al.; Loss of nicotinic receptors in monkey striatum after 1-methyl-4-phenyl-1,2,3,6-tetrahydropyridine treatment is due to a decline in oconotoxin Mil sites; Molecular Pharmacology; 61(1); pp. 230-238; Jan. 1, 2002.
Kumar et al.; Levodopa-dyskinesia incidence by age of Parkinson's disease onset; Movement disorders; 20(3); pp. 342-344; Mar. 2005.
Kydonieus et al. (Editors); Biochemical Modulation of Skin Reactions; CRC Press; Boca Ratan, FL; pp. 9-10; Dec. 1999.
Labrecque, G. et al.; Chronopharmacokinetics; Pharmaceutical News; 4(2); pp. 17-21; (year of pub. sufficiently earlier than effective US filing date and any foreign priority date) 1997.
Lai et al.; Long-term nicotine treatment decreases striatal a6* nicotinic acetylcholine receptor sites and function in mice; Molecular Pharmacology; 67(5); pp. 1639-1647; May 1, 2005.
Lai et al.; Selective recovery of striatal 1251-a-conotoxinMII nicotinic receptors after nigrostriatal damage in monkeys; Neuroscience; 127(2); pp. 399-408; Dec. 31, 2004.
Lamberg; Chronotherapeutics: Implications for drug therapy; American Pharmacy; NS31(11); pp. 20-23; Nov. 1991.
Langston et al.; Investigating levodopa-induced dyskinesias in the parkinsonian primate; Annals of Neurology; 47(4 Suppl 1); pp. S79-S88; Apr. 2000.
Laser et al.; A review of micropumps; J. of Micromech. And Microeng.; 14; pp. R35-R64; Apr. 2004.

(56) References Cited

OTHER PUBLICATIONS

Lemay et al.; Lack of efficacy of a nicotine transdermal treatment on motor and cognitive deficits in Parkinson's disease; Prog Neuropsychopharmacol Biol Psychiatry; 28(1); pp. 31-39; Jan. 2004.

Lemmer; Clinical Chronopharmacology: The Importance of Time in Drug Treatment, in Ciba Foundation Symposium 183—Circadian Clocks and their Adjustment (eds. Chadwick and Ackrill); John Wiley & Sons, Inc.; pp. 235-253; Apr. 1995.

Lemmer; Implications of chronopharmacokinetics for drug delivery: antiasthmatics, H2-blockers and cardiovascular active drugs; Adv Drug Del Rev; 6(1); pp. 83-100; Jan./Feb. 1991.

Lemmer; The clinical relevance of chronopharmacology in therapeutics; Pharmacological Research; 33(2); pp. 107-115; Feb. 1996.

LeWitt et al.; New developments in levodopa therapy; Neurology; 62(No. 1, Suppl. 1); pp. S9-S16; Jan. 2004.

Lieber Man; Compressed tablets by direct compression; Pharmaceutical Dosage forms; vol. 1, 2nd ed.; Marcel Dekker Inc.; pp. 195-246; (year of pub sufficiently earlier than effective US filing date and any foreign priority date) 1989.

Lieberman; Compression—coated and layer tablets; Pharmaceutical Dosage forms; vol. 1, 2nd ed.; Marcel Dekker Inc.; pp. 266-271; (year of pub, sufficiently earlier than effective US filing date and any foreign priority dale) 1989.

Lundbald el al.; Cellular and behavioural effects of the adenosine A2a receptor antagonist KW-6002 in a rat model of I-DOPA-induces Dyskinesia; Journal of Neurochemistry; 84(6); pp. 1398-1410; Mar. 2003.

Madandla et al,; Voluntary running provides neuroprotection in rats after 6-hydroxydopamine injection into the medial forebrain bundle; Metabolic Brain Disease; 19(1-2); pp. 43-50; Jun. 2004.

Maillefer et al.; A high-performance silicon micropump for an implantable drug delivery system; 12th IEEE Int'l Conf. on Micro Electro Mechanical Systems; MEMS '99; Orlando, FL; pp. 541-546; Jan. 1999.

McCallum et al,; Decrease in alpha3*/alpha6* nicotinic receptors in monkey brain after nigrostriatal damage; Molecular Pharmacology; 68(3); pp. 737-746; Sep. 2005.

McNeil Sweden AB. Package Leaflet: Information for the user Nicorette Microtab Lemon 2mg sublingual tablets. (This leaflet was last approved in Apr. 16, 2008). retrived from (www.lakemedelsverket.se/SPC_PIL/Pdf/enhumpil/Nicorette%20Microtab%20Lemon%202mg%20sublingual%20tablet%20ENG.pdf) Accessed Aug. 19, 2010.

Medtronic; MiniMed Paradigm® Veo(TM) System (product info.); retrieved May 12, 2015from the internet: (http://www.medtronic.co.uk/your-health/diabetes/device/insulin-pumps/paradigm-veo-pump/); 3 pgs.

Menzaghi et al.; Interactions between a novel cholinergic ion channel against, SIB-1765F anf L-DOPA in the reserpine model of parkinson's disease in rats; Journal of Pharmacology and Experimental Therapeutics; 280(1); pp. 393-401; Jan. 1, 1997.

MERCK manual of therapy and diagnosis; 17th edition. Merck Research Laboratories; pp. 1466-1471; (year of pub. sufficiently earlier than effective US filing date and any foreign priority date) 1999.

Meshul et al.; Nicotine Affects Striatal Glutamatergic Function in 6-OHDA Lesioned Rats; Advanced in behavioural Biology. Basal Ganglia VI.; Springer, Boston, MA.; vol. 54; pp. 589-598; (year of pub. sufficiently earlier than effective US filing date and any foreign priority date) 2002.

Meshul et al.; Nicotine alters striatal glutamate function and decreases the apomorphine-induced contralateral rotations in 6-OHDA-lesioned rats: Experimental Neurology; 175(1): pp. 257-274; May 31, 2002.

Molander et al.; Reduction of tobacco withdrawal symptoms with a sublingual nicotine tablet: A placebo controlled study; Nictonie & Tob. Res.; 2(2); pp. 187-191; May 2000.

Murphy et al.; Transdermal drug delivery systems and skin sensitivity reactions. Incidence and management; Am. J. Clin Dermatol.; 1(6); pp. 361-368; Nov./Dec. 2000.

Mutalik et al.; Glibenclamide transdermal patches: physicochemical, pharmacodynamic, and pharmacokinetic evaluation; J Pharm Sci; 93(6); pp. 1577-1594; Jun. 2004.

Nakadate et al.; Effects of chalcone derivatives on lipoxygenase and cyclooxygenase activities of mouse epidermis; Prostaglandins; 30(3); pp. 357-368; Sep. 1985.

National Institute of Neurological Disorders and Stroke. Parkinson's Disease: Hope Through Research. 54 pages; Retrieved from the internet (https://catalog.ninds.nih.gov/pubstatic//15-139/15-139.pdf) on Jan. 15, 2018.

Newmark; Plant phenolics as potential cancer prevention agents; Chapter 3 in Dietary Phytochemicals in Cancer Prevention; Chap. 3; Adv. Exp. Med. Biol. 401; pp. 25-34; © 1996.

Ohdo; Changes in toxicity and effectiveness with timing of drug administration: implications for drug safety; Drug Safety; 26(14); pp. 999-1010; Dec. 2003.

Olanow; The scientific basis for the current treatment of Parkinson's disease; Annu. Rev. Med.; 55; pp. 41-60; Feb. 18, 2004.

Olsson et al.; A valve-less planar pump in silicon; IEEE; The 8th International Conference on Solid-State Sensors and Actuators; vol. 2; pp. 291-294; Jun. 1995.

Olsson et al.; An improved valve-less pump fabricated using deep reactive ion etching; Proc. Of the IEEE, 9th Int'l Workshop on MEMS; San Diego, CA; pp. 479-484; Feb. 11-15, 1996.

O'Neill et al.; The role of neuronal nicotinic acetylcholine receptors in acute and chronic neurodegeneration: Current Drug Targets—CNS and Neurological Disorders; 1(4); pp. 399-412; Aug. 1, 2002.

Parkinson Study Group; Levodopa and the progression of Parkinson's disease; N Engl J Med.; 351; pp. 2498-2508; Dec. 9, 2004.

Petzinger et al.; Reliability and validity of a new global dyskinesia rating scale in the MPTP-lesioned non-human primate; Movement Disorders; 16(2); pp. 202-207: Mar. 1, 2001.

Priano et al.; Nocturnal anomalous movement reduction and sleep microstructure analysis in parkinsonian patients during 1-night transdermal apomorphine treatment; Neurol Sci.; 24(3); pp. 207-208; Oct. 2003.

Prosise et al.; Effect of abstinence from smoking on sleep and daytime sleepiness; Chest; 105(4); pp. 1136-1141; Apr. 1994.

Quik et al.; Differential alterations in nicotinic receptor a6 and /33 subunit messenger RNAs in monkey substantia nigra after nigrostriatal degeneration; Neuroscience; 100(1); pp. 63-72; Sep. 7, 2000.

Quik et al.; Differential declines in striatal nicotinic receptor subtype function after nigrostriatal damage in mice; Molecular Pharmacology; 63(5); pp. 1169-1179; May 1, 2003.

Quik et al.; Differential nicotinic receptor expression in monkey basal ganglia: Effects of nigrostriatal damage; Neuroscience; 112(3); pp. 619-630; Jul. 5, 2002.

Quik et al.; Expression of D3 receptor messenger RNA and binding sites in monkey striatum and substantia nigra after nigrostriatal degeneration: Effect of levodopa treatment.; Neuroscience; 98(2); pp. 263-273; Jun. 30, 2000.

Quik et al.: Increases in striatal preproenkephalin gene expression are associated with nigrostriatai damage but not L-DOPA-induced dyskinesias in the squirrel monkey; Neuroscience; 113(1): pp. 213-220; Aug. 2, 2002.

Quik et al.; L-DOPA treatment modulates nicotinic receptors in monkey striatum; Mol Pharmacol; 64(3); pp. 619-628; Sep. 2003.

Quik et al.; Localization of nicotinic receptor subunit mRNAs in monkey brain by in situ hybridization; The Journal of Comparative Neurology; 425(1); pp. 58-69; Sep. 11, 2000.

Quik et al.; Loss of a-conotoxinMII- and A85380-sensitive nicotinic receptors in Parkinson's disease striatum; Journal of Neurochemistry; 88(3); pp. 668-679; Feb. 1, 2004.

Quik et al.; Nicotine administration reduces striatal MPP+ levels in mice; Brain Research; 917(2); pp. 219-224; Nov. 2, 2001.

Quik et al.; Nicotine and nicotinic receptors; relevance to Parkinson's disease; Neurotoxicology; 23(4-5); pp. 581-594; Oct. 2002.

Quik et al.; Nicotinic receptors and Parkinson's disease; European Journal of Pharmacology; 393(1); pp. 223-230; Mar. 30, 2000.

(56) References Cited

OTHER PUBLICATIONS

Quik et al.; Subunit composition of nicotinic receptors in monkey striatum: Effect of treatments with 1-methyl-4-phenyl-1,2,3,6-tetrahydropyridine or L-DOPA; Molecular Pharmacology; 67(1): pp. 32-41; Jan. 2005.

Quik et al.; Vulnerability of 125I-a-conotoxin MiI binding sites to nigrostriatal damage in monkey; The Journal of Neuroscience; 21(15); pp. 5494-5500; Aug. 1, 2001.

Quik; Smoking, nicotine and Parkinson's disease; Trends in Neurosciences; 27 (9); pp. 561-568; Sep. 2004.

Redfern et al.; Circadian rhythms, jet lag, and chronobiotics: An overview; Chronobiology International; 11(4); pp. 253-265; Aug. 1994.

Reinberg; Concepts of Circadian Chronopharmacology; Annals of the New York Academy of Sciences; 618 (Temporal Control of Drug Delivery); pp. 102-115; Feb. 1991.

Rueter et al.; ABT-089: Pharmacological properties of a neuronal nicotinic acetylcholine receptor agonist for the potential treatment of cognitive disorders; CNS Drug Reviews; 10(2); pp. 167-182; Jun. 1, 2004.

Samii et al.; Parkinson's disease; The Lancet; 363(9423); pp. 1783-1793; May 29, 2004.

Schapria; Disease modification in Parkinson's disease; The Lancet Neurology; 3(6); pp. 362-368; Jun. 30, 2004.

Schneider et al.; Effects of SIB-1508Y, a novel neuronal nictonie acetylcholine receptor agonist, on motor behavior in parkinsonian monkeys; Movement Disorders; 13(4); pp. 637-642; Jul. 1, 1998.

Schneider et al.; Effects of the nicotinic acetylcholine receptor agonist SIB-1508Y on object retrieval performance in MPTP-treated monkeys: Comparison with levodopa treatment; Annals of Neurology; 43(3); pp. 311-317; Mar. 1, 1998.

Schober et al.; Classic toxin-induced animal models of Parkinson's disease; 6-OHDA and MPTP; Cell and Tissue Research; 318(1); pp. 215-224; Oct. 1, 2004.

Shin et al.; Enhanced bioavailability of triprolidine from the transdermal TPX matrix system in rabbits; Int. J. Pharm.; 234(1-2); pp. 67-73; Mar. 2002.

Silver et al.; Transdermal nicotine and haloperidol in Tourette's disorder: a double-blind placebo-controlled study; Journal of Clinical Psychiatry; 62(9); pp. 707-714; Sep. 1, 2001.

Singer et al.; Nightmares in patients with Alzheimer's disease caused by donepezil: Therapeutic effect depends on the time of intake; Nervenarzt; 76(9); pp. 1127-1129; Sep. 2005 (Article in German w/ Eng. Summary).

Star Micronics Co., Ltd; Prototype Diaphragm Micro Pump SDMP305 (specifications); retrieved May 12, 2015 from the internet archive as of Jul. 2006 (http://www.star-m.jp/eng/products/develop/de07.htm); 3 pgs.

Stocchi et al.; Motor fluctuations in levodopa treatment: clinical pharmacology; European Neurology; 36(Suppl 1); pp. 38-42; Jan. 1996.

Thiele et al. (Ed.); Oxidants and Antioxidants in Cutaneous Biology: Current Problems in Dermatology (Book 29); S. Karger; 196 pgs.; Feb. 2001.

Togasaki et al.; Dyskinesias in normal squirrel monkeys induced by nomifensine and levodopa; Neuropharmacology; 48(3); pp. 398-405; Mar. 31, 2005.

Togasaki et al.; Levodopa induces dyskinesias in normal squirrel monkeys; Annals of Neurology; 50(2); pp. 254-257; Aug. 1, 2001.

Togasaki et al.; The Webcam system: A simple, automated, computer-based video system for quantitative measurement of movement of nonhuman primates; Journal of Neuroscience Methods: 145(1); pp. 159-166; Jun. 30, 2005.

Tolosa et al.; Antagonism by piperidine of levodopa effects in Parkinson disease; Neurology; 27(9); pp. 875-877; Sep. 1, 1977.

U.S. Department of Health and Human Services, Food and Drug Administration, Center for Drug Evaluation and Research (CDER); Guidance for industry: Abuse-deterrent opioids-Evaluation and labeling; 24 pages; retrieved from the internet (http//www.fda.gov/downloads/drugs/guidancecomplainceregulatoryinformation/guidances/ucm344743.pdf); Jan. 2013.

United States of America VA/DoD; Tapering and discontinuing opioids; 2 pages; retrieved from the internet (http://www.healthquality.va.gov/guidelines/Pain/cot/OpioidTaperingFactSheet23May2013v1.pdf), on Sep. 1, 2016.

Vieregge et al.; Transdermal nicotine in PD: A randomized, double-blind, placebo-controlled study; Neurology; 57(6); pp. 1032-1035; Sep. 25, 2001.

Villafane et al.; Long-term nicotine administration can improve Parkinson's disease: report of a case after three years of treatment; Revista Neuroiogica Argentina; 27(2); pp. 95-97; (year of pub. sufficiently earlier than effective US filing date and any foreign priority date) 2002.

Warburton et al.; Facilitation of learning and state dependency with nicotine; Psychoparmacology; 89(1); pp. 55-59; May 1, 1986.

Wermuth et al.: Glossary of terms used in medicinal chemistry Pure & Appl. Chem., vol. 70(5); 1129-1143; 1998 AC recommendations 1998): Pure and Applied Chemistry; 70(5); pp. 1129-1143; Jan. 1998.

Wesnes et al.; Effects of scopolamine and nicotine on human rapid information processing performance; Psychoparmacology; 82(3); pp. 147-150; Sep. 1, 1984.

Westman et al.; Oral nicotine solution for smoking cessation: a pilot tolerability study; Nicotine and Tobacco Research; 3(4); pp. 391-396; Nov. 1, 2001.

Wille et al.; cis-urocanic Acid Induces Mast Cell Degranulation and Release of Preformed TNF-alpha: A Possible Mechanism Linking UVB and cis-urocanic Acid to Immunosuppression of Contact Hypersensitivity; Skin Pharm Appl Skin Physiol; 12(1-2); pp. 18-27; Jan. 1999.

Wille et al.; Inhibition of irritation and contact hypersensitivity by ethacrynic acid; Skin Pharm Appl Skin Physiol; 11(4-5); pp. 279-288; Jul. 1998.

Wille et al.; Inhibition of Irritation and Contact Hypersensitivity by Phenoxyacetic Acid Methyl Ester in Mice; Skin Pharm Appl Skin Physiol; 13(2); pp. 65-74; Mar. 2000.

Wille et al.; Several different ion channel modulators abrogate contact hypersensitivity in mice; Skin Pharm Appl Skin Physiol; 12(1-2); pp. 12-17; Jan. 1999.

Wille, J.; Novel topical delivery system for plant derived hydrophobic anti-irritant active (presentation abstract No. 273); 226th ACS National Meeting: New York, NY; Sep. 7-11, 2003.

Wille; In Closing: an editorial on Plant-Derived Anti-irritants. Cosmetics & Toiletries, 118 (8), Aug. 2003.

Wille; Novel plant-derived anti-irritants; (presented Dec. 5-6, 2002 at the 2002 Ann. Scientific Mtg. & Tech. Showcase); J. Cosmet. Sci.; 54; pp. 106-107; Jan./Feb. 2003.

Wille; Thixogel: Novel topical delivery system for hydrophobic plan actives; in ROSEN (Ed.) Delivery System Handbook for Personal Care and Cosmetic Products; 1st Ed.; ISBN: 978-0-8155-1504-3; pp. 762-794; Sep. 2005.

Youan; Chronopharmaceutics: gimmick or clinically relevant approach to drug delivery?; J Cont Rel; 98(3); pp. 337-353; Aug. 2004.

Yun et al.; A distributed memory MIMD multi-computer with reconfigurable custom computing capabilities; IEEE; Proc. Int'l. Conf. on Parallel and Distributed Systems; pp. 8-13; Dec. 10-13, 1997.

Zubieta et al.; Placebo effects mediated by endogenous opioid activity on mu-opioid receptors; 25(34); pp. 7754-7762; Aug. 24, 2005.

Arora et al.; U.S. Appl. No. 16/474,083 entitled "Methods and devices for treating levodopa induced dyskinesia," filed Jan. 15, 2020.

Zumbrunn et al.; U.S. Appl. No. 16/933,836 entitled "Transdermal drug delivery method and system," filed Jul. 20, 2020.

Ruane et al.; U.S. Appl. No. 17/293,570 entitled "Thermally regulated transdermal drug delivery system," filed May 13, 2021.

BIOSYNCHRONOUS TRANSDERMAL DRUG DELIVERY

CROSS REFERENCE TO RELATED APPLICATIONS

This application is a continuation of U.S. patent application Ser. No. 15/385,665, filed Dec. 20, 2016, titled "BIOSYNCHRONOUS TRANSDERMAL DRUG DELIVERY," which is a continuation of U.S. patent application Ser. No. 14/746,704, filed Jun. 22, 2015, titled "BIOSYNCHRONOUS TRANSDERMAL DRUG DELIVERY," now U.S. Pat. No. 9,555,227, which is a continuation of U.S. patent application Ser. No. 14/162,156 filed Jan. 23, 2014, titled "BIOSYNCHRONOUS TRANSDERMAL DRUG DELIVERY," which is a continuation of U.S. patent application Ser. No. 11/162,517 filed Sep. 13, 2005, titled "BIOSYNCHRONOUS TRANSDERMAL DRUG DELIVERY," which claims the benefit of U.S. Provisional Application No. 60/609,418 filed Sep. 13, 2004, titled "BIOSYNCHRONOUS TRANSDERMAL DRUG DELIVERY," each of which are incorporated herein by reference.

This application also relates to PCT application No. PCT/IB2004/002947 entitled Transdermal Drug Delivery Method and System filed Sep. 13, 2004 which is incorporated herein by reference.

FIELD OF THE INVENTION

The present invention relates, in general, to controlled drug delivery methods and systems, and, more specifically, to systems and methods for bisynchronous transdermal drug delivery in which drugs, pharmaceuticals, and other bioactive substances are delivered transdermally into a body in a manner that is synchronized with biological processes and/or biological rhythms so as to improve performance of the substance in the body.

Relevant Background

In the field of drug delivery, it is recognized that supplying the drug in a correct temporal pattern is an important attribute of any drug delivery methodology. Controlled release drug delivery systems are intended to improve response to a drug and/or lessen side effects of a drug. The term "controlled release" refers generally to delivery mechanisms that make an active ingredient available to the biological system of a host in a manner that supplies the drug according to a desired temporal pattern. Controlled release drug delivery may be implemented using instantaneous release systems, delayed release systems, and sustained release systems. In most cases, controlled release systems are designed to maintain a sustained plasma level of an active ingredient in a drug within a human or animal host over a period of time.

Instantaneous release refers to systems that make the active ingredient available immediately after administration to the biosystem of the host. Instantaneous release systems include continuous or pulsed intravenous infusion or injections. Such systems provide a great deal of control because administration can be both instantaneously started and stopped and the delivery rate can be controlled with great precision. However, the administration is undesirably invasive as they involve administration via a puncture needle or catheter. 'Delayed release' refers to systems in which the active ingredient made available to the host at some time after administration. Such systems include oral as well as injectable drugs in which the active ingredient is coated or encapsulated with a substance that dissolves at a known rate so as to release the active ingredient after the delay. Unfortunately, it is often difficult to control the degradation of the coating or encapsulant after administration and the actual performance will vary from patient to patient. Sustained Release generally refers to release of active ingredient such that the level of active ingredient available to the host is maintained at some level over a period of time Like delayed release systems, sustained release systems are difficult to control and exhibit variability from patient to patient. Due to the adsorption through the gastrointestinal tract, drug concentrations rise quickly in the body when taking a pill, but the decrease is dependent on excretion and metabolism, which cannot be controlled. In addition, the adsorption through the gastrointestinal tract in many cases leads to considerable side effects (such as ulcers), and can severely damage the liver.

Transdermal drug delivery has developed primarily for sustained release of drugs in situations where oral sustained release systems are inadequate. In some cases, drugs cannot be effectively administered orally because the active ingredients are destroyed or altered by the gastrointestinal system. In other cases the drug may be physically or chemically incompatible with the coatings and/or chelating agents used to implement sustained release. In other cases a transdermal delivery system may provide sustained release over a period of days or weeks whereas orally administered drugs may offer sustained performance over only a few hours. A wide variety of active substances can be delivered through transdermal systems so long as the active substance can be provided in a form that can cross the skin barrier.

In most cases transdermal delivery systems are passive, taking the form of a patch that is adhesively attached to the host. The patch includes a quantity of the active substance, along with a suitable carrier if need be, absorbed in a sponge or similar system. Once applied, the active ingredient diffuses into the host through the skin at a rate determined by the concentration of the active substance and the diffusivity of the active substance. However, a variety of physical and chemical processes at the skin/patch boundary affect the delivery rate and may eventually inhibit drug delivery altogether. Active transdermal delivery systems have been developed to help regulate the delivery rate by providing mechanisms to improve drug delivery over time by "pumping" the active ingredient. One such system is described in U.S. Pat. No. 5,370,635 entitled "DEVICE FOR DELIVERING A MEDICAMENT" which describes a system for delivering a medicament and dispensing it to an organism for a relatively long period of time, for example at least a few days. The device can be adapted for positioning on the surface of the skin of a human or possibly an animal body in order to apply a medicament thereto from the outer side thereof.

Conventional transdermal systems circumvent the disadvantages of the adsorption through the gastrointestinal tract, but they do not optimize or tailor the dosing regimen to offset peak symptoms. In addition the constant transdermal delivery of a drug can lead to severe side effects, including debilitating sleep disorders and ever increasing tolerance.

Timed delivery is most often used to maintain a sustained level of a drug in the body. A significant focus of current research in drug delivery has been to determine the influence of a patient's circadian or other biological rhythms on drug efficacy and efficiency. This research demonstrates that certain disease symptoms follow a daily pattern, with peak symptoms at certain times of the day. It has been widely acknowledged that hormones, neurotransmitters and other intra-body compounds are released in different amounts at different times of the day pursuant to daily patterns. The Wall Street Journal reported on May 27, 2003 that "Doctors are increasingly looking at the clock when it comes to prescribing medicine, instructing patients not only to what drug to use but also precisely when to take it. The new approach stems from a growing body of research that demonstrates that certain diseases tend to get worse at certain times of the day. By synchronizing medications with a patient's body clock, many physicians believe that the drugs will work more effectively and with fewer side effects. In some cases, the improvements have been so pronounced that doctors have been able to reduce dosages." Similarly, American Pharmacy reports that "Circadian physiologic processes alter drug absorption, distribution, metabolism, and excretion. As a result, drug doses need to be adjusted to meet the differing needs of target organs or tissues at various times of the day." See, L. Lamberg, American Pharmacy, 1991; N831(11): 20-23. Doctors have responded to this growing body of research by prescribing a carefully timed drug administration regimen to optimize treatment.

Recently, an orally administered drug for arthritis treatment has suggested a chronotherapeutic approach using a delay release system where the delay is scheduled to release the active ingredient at the beginning of an interleukin 6 cascade that is believed to cause early morning stiffness in rheumatoid arthritis patients. By attempting to synchronize the drug delivery with a biological cycle it is believed that low doses may be used to achieve desired results. However, this system does not overcome the limitations of delayed release systems described above. Although it is possible to meet the requirements of chronopharmacology with pills, this requires an enormous amount of discipline by the patient to comply with the treatment regimen. As illustrated above, to achieve optimal results, many patients may need to wake up during the night to take their medication.

Hence, what is needed is a reliable means of delivering multiple drugs in precisely timed and measured doses-without the inconvenience and hazard of injection, yet with improved performance as compared to orally-delivered drugs.

Currently, patient compliance (taking the proper dosages at the prescribed times) is a critical problem facing caregivers and pharmaceutical firms alike. Studies show that only about half of patients take medications at the times and in the dosages directed by their physician. It is reported that each year, 125,000 deaths and up to 20% of all hospital and nursing home admissions result from patient non-compliance. It is estimated that non-compliance results in additional healthcare costs in excess of $100 billion per year in United States. These figures are even more pronounced for the elderly. Hence, a need exists for systems and methods that increase patient compliance for administration of a variety of drugs.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

SUMMARY OF THE INVENTION

Briefly stated, the present invention involves synchronizing the administration of compounds with the human body's natural circadian rhythms and addiction rhythms to counteract symptoms when they are likely to be at their worst by using an automated and pre programmable transdermal or other drug administration system.

Specifically, this invention describes a method to maximize the efficiency of compound administration, decrease negative side effects and increase the efficacy of pharmacological therapy by synchronizing and tailoring the administration of certain compounds to match these circadian rhythms.

Thus based on an analysis of the human body's circadian rhythms, the invention delivers varying dosages at varying times, pursuant to a preprogrammed dosage profile. This ensures that peak drug concentrations are present in the bloodstream to offset peak disease and addiction symptoms arising from variances and fluctuation in the body's natural circadian rhythms. Further, these methods ensure that less of a drug is in the bloodstream when disease and addiction symptoms are at their lowest.

The present invention describes methods for treating diseases, addictions and disorders in humans. These methods involve synchronizing and tailoring the administration of compounds with the body's natural circadian rhythms to counteract symptoms when they are likely to be at their worst by using an automated and pre programmable transdermal drug administration system.

More specifically, these methods synchronize and tailor drug administration to the human body's circadian rhythms to deliver varying dosages at varying times. This ensures that peak drug concentrations are present in the bloodstream to offset peak disease and addiction symptoms arising from variances and fluctuation in the body's natural circadian rhythms. Further, these methods ensure that less of a drug is in the bloodstream when disease and addiction symptoms are at their lowest. This minimizes negative side effects, and increases efficacy of the dosing regimen.

DETAILED DESCRIPTION OF THE PREFERRED EMBODIMENTS

Figure 1:
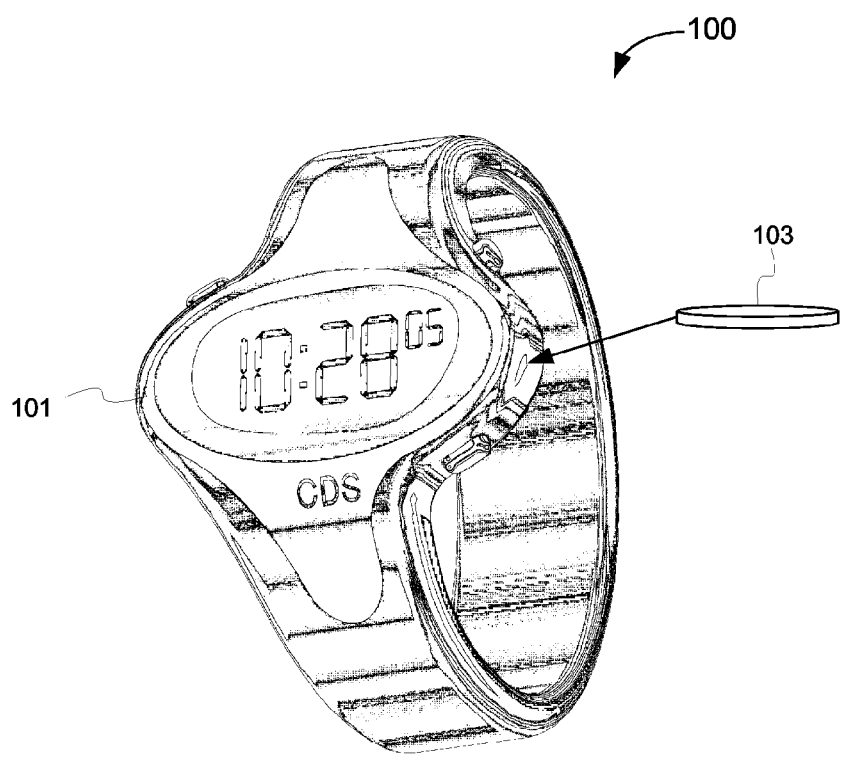
FIG. 1 shows an exemplary device useful for implementing the present invention.

The reality of circadian rhythms in animals including humans is well known. Biological rhythms are periodic fluctuations in biological characteristics over time, which also include circadian as well as seasonal variations. Circadian, or approximately 24-hour, rhythms include the production of biological molecules such as cortisol and adrenaline, the regulation of body temperature and heart rate, changes in characteristics of blood, such as stickiness, and behaviors such as wakefulness, sleep and periods of activity.

Research demonstrates that certain disease symptoms follow a daily pattern, with peak symptoms at certain times of the day. It has been widely acknowledged that hormones, neurotransmitters and other intra-body compounds are released in different amounts at different times of the day pursuant to daily patterns. It is believed that the failure of current transdermal systems to synchronize drug administration with the body's natural rhythms often lead to (i) severe side effects, including debilitating sleep disorders (in the context of nighttime nicotine administration, for example), (ii) ever increasing tolerance (in the case of nitroglycerin and other pharmaceuticals for example), (iii) more expensive therapies, since more of a compound is needed since body rhythm tailored dosing is not implemented. In addition, many addictions follow a daily pattern consistent with one's circadian rhythms. For example, according to studies performed, immediately upon waking, smokers have peak nicotine cravings. These peak cravings return after each meal, due to the interplay of serotonin release as a trained response to the culmination of a meal. Our methods precisely time the administration of drugs so that they reach peak levels when symptoms are likely to be at their worst, and efficacy is greatly improved.

The present invention involves precisely timing the administration of drugs so that they reach peak levels in synchronization with times when symptoms are likely to be at their worst, or times at which the drugs are believed to be more effective in the body and/or better tolerated by the patient. The present invention is described in terms of a particular example drug delivery system that provides automated and precise control over dosing, with single-dose capability, (once while people sleep) or capability to administer separate and varying-sized doses many times throughout a multiple day period. The particular implementation is consistent with a commercial development of a miniaturized, automated and programmable non-invasive drug delivery system called the ChronoDose™ system being developed by the assignee of the present invention. The system enables controlling of the amount of drug exposed to the skin in a controlled time dependent way according to a programmed administration schedule that implements a desired dosage profile. In this manner the present invention enables one to precisely control and vary the time of drug release and the amount of each dose, pursuant to an easily set preprogrammed dosage profile.

Research demonstrates that for certain symptoms, conditions and diseases, drug effects can be optimized when administered in a defined (and often varying) dosage at predefined times. This is known as Chrono-Pharmacology. To illustrate the importance of Chrono-Pharmacology consider the following facts:

Asthma attacks are 100 times more likely between 4:00 and 6:00 A.M.

Heart attacks and strokes are most likely to occur around 6:00 A.M.

Variant Angina attacks occur 30 times more often in the middle of the night between 2:00 A.M. and 4:00 A.M.

Smokers experience the highest cravings immediately upon waking up.

Lethargy and difficulty getting out of bed is highest immediately upon waking up early in the morning.

Cold and flu symptoms peak during night time and early morning hours, when cold medications are wearing off.

In accordance with the present invention, substances with proven or suspected chrono-pharmacological efficiency are integrated into a miniaturized, automated, programmable watch-like device, such as device 100 shown in FIG. 1. The delivery system 100 shown in FIG. 1 can be used for a variety of active compositions, and is small, fully automated and programmable. This system consists of a re-usable wristwatch-like device 101 to control the time and dosage of drug delivery; and a small, disposable, 'reservoir' 103, which is about the size of a quarter or ½ dollar coin in a particular example, that the user can simply pop-in to place on the watch-like platform. This reservoir patch lasts, for example, up to 72 hours, depending on the application. Shorter and longer reservoir lifetimes are contemplated. The device is readily adapted to be worn on the forearm, ankle, or other convenient body location.

In a particular application the replaceable reservoir can include a description of an administration schedule that can be used to manually or automatically program device 100 with an administration schedule. For example, written schedule can be printed on or affixed to the reservoir 101 or electrically programmed using volatile or non-volatile memory. In this manner a dosing profile can be prescribed and filled by a pharmacy in much the same manner as a conventional drug prescription is handled today.

Figure 3:
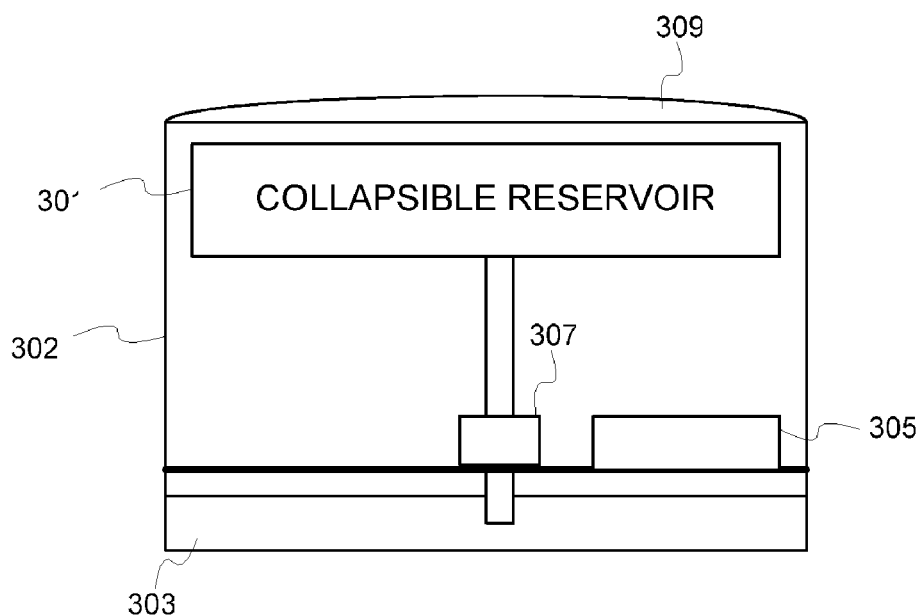
FIG. 3 is a schematic illustration of a drug delivery device in accordance with the present invention.

An exemplary implementation shown in FIG. 3 comprises a collapsible drug reservoir, an expandable waste reservoir, a micro-pump, electronics for automation, a display, and a highly permeable membrane. An exemplary system is described in PCT application No. PCT/IB2004/002947 entitled TRANSDERMAL DRUG DELIVERY METHOD AND SYSTEM filed Sep. 13, 2004 which is incorporated herein by reference. The drug reservoir will contain about 3 ml of drug formulation. A tiny, miniaturized pump is activated at preprogrammed times and releases a predefined amount of drug formulation into the drug chamber, where the formulation comes into contact with highly permeable membrane. This membrane rests on the skin, and provides for even diffusion of the drug over the device's drug absorption surface area. This membrane works effectively with, and can be coated with, an adhesive. In operation, when the administration of the drug needs to be discontinued, the remaining drug formulation is either removed from the membrane area via a waste chamber, containing a hydrophilic substance (hydrogel) or the device is taken off.

Figure 4:
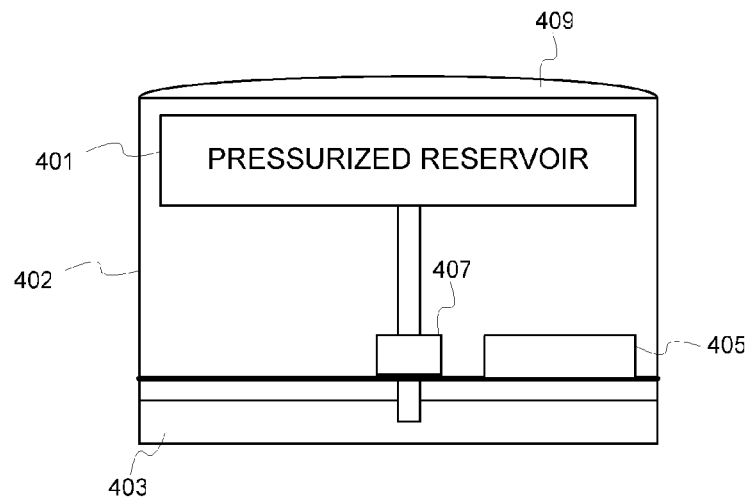
FIG. 4 is a schematic illustration of an alternative drug delivery device in accordance with the present invention.

In an implementation shown in FIG. 4, a pressurized drug reservoir is used which minimizes or eliminates need for a micropump. Electronics control a valve that allows controlled quantities of the drug to be applied to the drug chamber where the formulation comes into contact with highly permeable membrane.

The construction and use of transdermal patches for the delivery of pharmaceutical agents is known. See, for example, U.S. Pat. No. 5,370,635 entitled "DEVICE FOR DELIVERING A MEDICAMENT" the disclosure of which is incorporated herein by reference. Such patches may be constructed using a saturated media, pressurized reservoirs, or unpressurized reservoirs with micropumps for continuous, pulsatile, or on-demand delivery of an active material. For example, a pharmaceutically acceptable composition of an active material may be combined with skin penetration enhancers including, but not limited to, oleic acid, amino acids, oleyl alcohol, long chain fatty acids, propylene glycol, polyethylene glycol, isopropanol, ethoxydiglycol, sodium xylene sulfonate, ethanol, N-methylpyrrolidone, laurocapram, alkanecarboxylic acids, dimethylsulfoxide, polar lipids, N-methyl-2-pyrrolidone, and the like, which increase the permeability of the skin to the active material and permit the active material to penetrate through the skin and into the bloodstream. Pharmaceutically acceptable compositions may be combined with one or more agents including, but not limited to, alcohols, moisturizers, humectants, oils, emulsifiers, thickeners, thinners, surface active agents, fragrances, preservatives, antioxidants, vitamins, or minerals. Pharmaceutically acceptable compositions may also be combined with a polymeric substance including, but not limited to, ethylcellulose, hydroxypropyl cellulose, ethylene/vinylacetate, polyvinyl pyrrolidone, and the like, to provide the composition in gel form, which may be dissolved in solvent such as methylene chloride, evaporated to the desired viscosity, and then applied to backing material to provide a patch. The backing can be any of the conventional materials such as polyethylene, ethyl-vinyl acetate copolymer, polyurethane and the like.

Example substances include caffeine and a variety of over-the-counter and prescription stimulants (for treating fatigue, sleep disorders, attention deficit disorders and a variety of other conditions), nicotine (for smoking cessation), nitroglycerin (for treating heart attack and strokes), fentanyl (for treating chronic pain), albutamol (for treating asthma), and selegiline (for treating depression, attention deficit disorder or Parkinson's disease). We have carefully identified these specific drugs and diseases because they have the following attributes: (i) Chrono-Pharmacology is critical to optimized dosing but is not being implemented because no automated transdermal system exists, and (ii) these drugs can be transdermally absorbed passively (i.e., without the need for ultrasound or electrical stimulation or other permeation enhancers). Exemplary chrono-pharmacological systems that can make use of the present invention are summarized in Table 1.

| DISEASES/ CONDITION | CHRONOPHARMACOLOGY |
|---|---|
| Morning Lethargy | Adrenaline is lowest in the morning, making waking uncomfortable and difficult for many people. This can be treated by administering OTC Stimulant before waking |
| Smoking Cessation | Nicotine at night creates sleeping disorders (nightmares), but cravings are the highest after waking up. This can be treated by administering Nicotine before waking up. |
| Angina | Angina (variant) attacks occur 30 (thirty) times more often between 2:00 a.m. and 4:00 a.m. This can be treated by administering larger nitroglycerin doses in early morning |
| Asthma | Asthma attacks are 100 times more likely between 4:00 a.m. and 6:00 a.m. Adrenaline and Cortisol are virtually absent at night. This can be treated by administering albutamol in early morning |
| Colds and Flu | Heaviest symptoms overnight and in the morning. This can be treated by administering Cold/Flu medicine during the night. |
| Heart Attacks and Strokes | Heart attacks and strokes are most likely between 6:00 a.m. and Noon. This can be treated by administering Anticoagulants before waking up. |
| Pain | Neurological pain is worst between 3 A.M and 8 A.M. This can be treated by administering pain medication during sleep. |
| Depression | Selegiline at night can create sleeping disorders (nightmares), but depression symptoms are high immediately upon waking up. This can be treated by administering Selegiline before waking up. |
| Rheumatoid Arthritis | Worst upon awakening. Cortisol and anti-inflammatory hormones are very low at night This can be treated by administering medication delivered before waking up. |
| Supplements | Vitamins and supplements are best administered in low doses over the course of the day to be most effective. |

Using this system the present invention can pre-program the times and amount of each dosage by precisely controlling the amount of drug exposed to the skin during each dosing. This feature is advantageous when a drug is best administered during sleep, e.g., 1 to 2 hours before waking up. The present invention precisely counteracts peak disease symptoms and increase patient compliance.

Figure 2A:
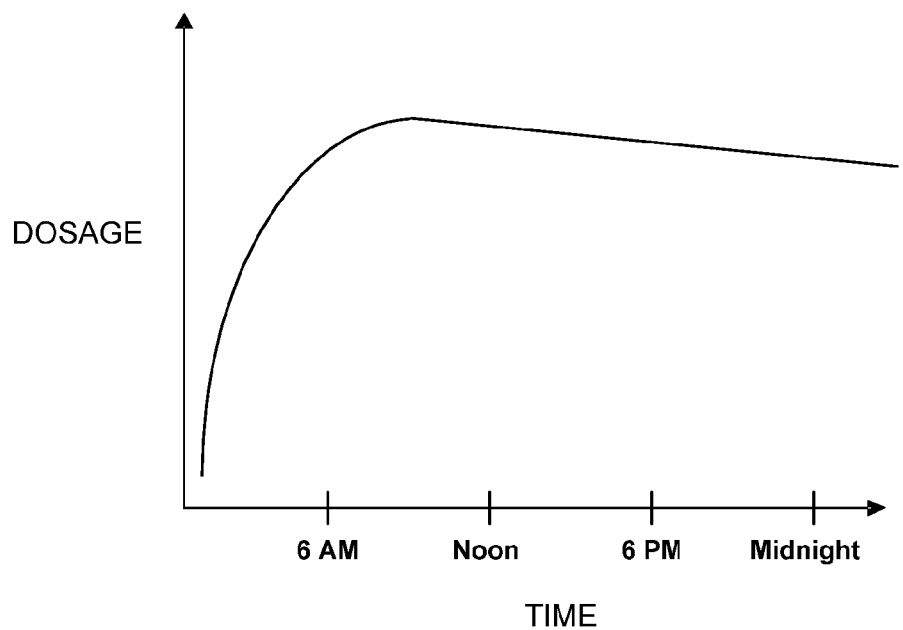
FIG. 2A and FIG. 2B illustrate comparative drug release profiles demonstrating operation of the present invention.
Figure 2B:
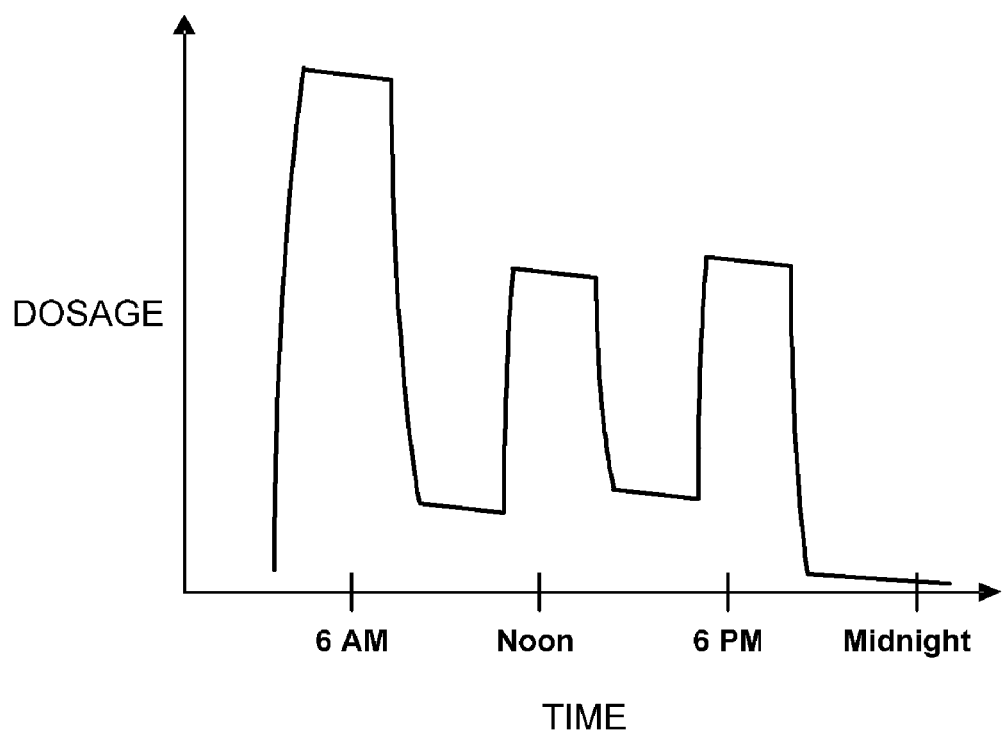

The present invention represents the first true non-invasive chrono-pharmacological drug delivery device. While current transdermal applications are restricted to the dosage profile shown in FIG. 2A, the automated implementation of the present invention can be programmed for a variety of drug delivery patterns to achieve customized patient dosing regiments for optimal therapy (FIG. 2B). There are many advantages for a controlled transdermal release of an active material such as a drug. As used herein, the term 'controlled' or 'sustained' release of an active material includes continuous or discontinuous, linear or non-linear release of the active material according to a programmed schedule. Among the advantages of controlled release are the convenience of a single application for the patient, avoidance of peaks and valleys in systemic concentration which can be associated with repeated injections, the potential to reduce the overall dosage of the active material, lower body stress, and the potential to enhance the pharmacological effects of the active material. A lower, sustained dose can also prevent adverse effects that are occasionally observed with infusion therapy. In addition to significantly reducing the cost of care, controlled release drug therapy can free the patient from repeated treatment or hospitalization, thus offering the patient greater flexibility and improving patient compliance. A controlled release formulation of certain drugs also provides an opportunity to use the drug in a manner not previously exploited or considered. The present invention is particularly advantageous when (i) known chrono-pharmacological information shows that a drug's effects can optimized when administered in a defined dosage at a predefined time or times, and/or (ii) patient compliance with the dosing regimen is greatly increased due to automation, (doses required at inopportune times, when sleeping, for example).

A device according to the present invention in general comprises dispensing means, e.g., a pump, at least one drug reservoir, at least one administration element (patch reservoir, administration reservoir, administration compartment, administration chamber) and at least one solvent removal and/or recovery element and if necessary control means interconnected to each other. In a preferred embodiment of the invention the administration reservoir and the solvent recovery means are incorporated in an administration unit (patch). The at least one drug reservoir contains a sufficient amount of one or more active substance dissolved or dispersed at an appropriate concentration in a formulation which may contain a solvent or a solvent mixture that is volatile. If appropriate other excipients, for example tissue permeation promoters (enhancers), thickening substances, solubilizers, buffers, chemical stabilizers, preservatives are present too.

The active substance may be any dispensable fluid (for example a liquid, gel or powder), although liquids are particularly of use in the dispensing unit. In some embodiments, at least one of the reservoirs may contain an active substance in powder or other dry form. The powder or other agent is dispensed from the reservoir, and may be combined with a solvent and/or another liquid such as a penetration enhancer. If appropriate the dispensing unit may allow chemical reactions to occur, e.g., in the administration reservoir, as well as phase changes to stabilize (such as a change from a solid to a liquid state).

In operation the formulation contained in the at least one drug reservoir is dispensed by the dispensing unit into the at least one administration reservoir (patch reservoir). Volume and frequency of administration of the active substance are controlled by a control unit which preferably is freely programmable according to given needs. The solvent recovery means reclaim solvent that was dispensed together with the formulation into the patch reservoir and is not absorbed. The preferably volatile solvent evaporates from the interface continuously and is guided to the solvent recovery means. If appropriate a heating element or other helping means may be used for supporting evaporation of the solvent. However the temperature of the skin in general is sufficient. The solvent recovery means serve to remove depleted solvent from the interface such that, e.g., after repeated dispensing, active substance concentration maintains at a certain concentration and no unwanted substance is accumulated within the device. Upon quitting dispensing of formula, the residual solvent is recovered and dryness of the interface is achieved, which results in controlled termination of drug delivery. Alternatively or in addition depleted solvent may be discharged into environment only, e.g., by direct evaporation.

In general the active substance is completely enclosed in the administration/patch reservoir and is not in contact with the environment or other components. The interface may comprise a membrane (polymer membrane) which may be lined with an absorbent material, such as blotting paper, suitable to receive active substance and facing inwards to the interior of the device. The membrane of the interface is in functional contact with the surface to be treated. The drug formulation is dispensed onto the interface by the dispensing unit which is interconnected to the drug reservoir. The solvent recovery means are normally arranged at a certain distance from the absorbent material preventing uncontrolled absorption of solvent. The volume and frequency of dispensing are freely programmable and are used to control the delivery rate and the time pattern of delivery of the drug.

Drug is delivered from the interface primarily by diffusion. The solvent recovery element reclaims the solvent that was dispensed with the formulation onto the interface and was not absorbed otherwise. The solvent recovery element preferably is located within the device and comprises one or more desiccants and/or general adsorbents such as silica gel, molecular sieves or active carbon. These materials are normally arranged within a bag consisting of non-wettable but vapor permeable material e.g., such as GoreTex®. In a preferred embodiment the solvent recovery element is arranged close to but in non-contact with the interface. The volatile solvent evaporates from the interface continuously under the influence of body heat and the vapors are trapped in the solvent recovery element. The solvent recovery element serves the purpose of removing depleted solvent from the interface so that, after repeated dispensing, drug concentration maintains its highest value and no freely moving liquid is formed within the device. Upon quitting dispensing of drug formula, the residual solvent is recovered and dryness of the interface is achieved, which brings about stoppage of drug delivery. The solvent recovery element is contained in a non-wettable material in order to avoid uptake of drug formula and consequent loss of drug.

Several parameters are relevant for the amount of active substance absorbed by the surface to be treated such as concentration of the active substance in the solvent, the repetition-rate of supply and the volume supplied. These parameters are controllable by the described invention.

Solvent that is not absorbed by the skin in a sufficient way is carried off in another way than by absorption through the skin, e.g., by evaporation into the environment and/or by absorption by another means, e.g., absorbing substance such as silica gel. By this it is possible to avoid negative decrease of the concentration of active substance due to accumulation of the solvent which would impact the diffusion rate through the skin. Especially solvents based on water and/or alcohol are having at temperatures nearby the temperature of skin a vapor pressure which is sufficiently high to carry off the solvent by evaporation. However, the carrying off and/or diffusion rate of the solvent preferably is adjusted to the diffusion rate of the active substance through the skin to avoid accumulation of the solvent or precipitation of the active substance on the skin in a negative way.

The described invention offers the opportunity to precisely control the rate and the time pattern of systemic drug delivery. It can be applied to the delivery of drug into and/or across the skin. With the methodology according to the present invention the amount of active substance delivered per unit of time can be adjusted to values ranging between zero and a known maximum, the moments of time can be defined at which the delivery rate is set to a predetermined value and the delivery of drug over time spanning hours or days can be regulated in a programmed manner, e.g., using real time control. A device suitable to carry out the described technology offers the opportunity of fully automated transdermal drug delivery.

The method most widely used in prior art for automated controlled transdermal delivery is iontophoresis. With this method control of delivery of a drug is achieved by an electric current which is applied to the skin. By adjusting the current the delivery rate of the drug is regulated. Advantages of the present invention over iontophoresis are the ability to completely turn off delivery or reduce the delivery rate below a minimal value corresponding to passive skin permeation, the absence of skin irritation that the electric current may cause when applied to the skin and the low energy consumption compared to iontophoresis because normally no high currents are needed for extensive periods of time.

Conventional patch based delivery systems as known from prior art comprising a patch and a therewith interconnected dispensing unit are more or less suitable to administrate a chemical substance under a specific time regime, where the quantity of the specific dose delivered to the patch can be predetermined more or less accurate and each time period of dispensing the substance can be predetermined as well. However, turning delivery to a patch as known from prior art on and off causes uncontrolled time lag in the delivery rate to or through the skin. The delivery systems known from prior art often lead to a constantly diminishing dispensing rate. These problems are avoided by the present invention.

The disclosed invention offers a combination of formula dispensing with an on- and off-turning delivery of the formula and a simultaneous solvent recovery for the purpose of maintaining a constant and high drug delivery rate. The achievable delivery rate and the time lag due to on- and off-events result from the interplay between the rate of formula dispensing and the rate of solvent recovery. The former is preferably controlled by a freely programmable pump and the latter by amount and quality of the material of the solvent recovery element.

Precise control of delivery of the active substance is very important. Related thereto is the precise control of the solvent. The solvent may be controlled by additional means e.g., as described as follows.

A solvent removal system comprises a waste reservoir which is interconnected by a waste valve, e.g., a pinch valve, and/or a waste pump to the administration reservoir. In the case of a pin valve the waste valve preferably is driven by utilizing a wire made out of Shape-Memory-Alloy (SMA) or an alternative device pursuant to a preprogrammed regimen. In a given example the waste valve is opened or the waste pump is turned on such that the solvent is removed and e.g., brought in contact to a desiccant such that the solvent is safely absorbed. Proper administration may be achieved by opening and closing the connection to the waste reservoir by an appropriate time regime. In certain applications it is helpful to switch the connection to the waste reservoir with a certain delay with respect to the administration of the active substance. Instead or in addition to a pinch valve a micro pump may be appropriate to pump excessive solvent into a waste reservoir. In a further embodiment the tubing e.g., for depletion of solvent can comprise absorbent material which thereby is brought into direct contact with depleted carrier solution. It is possible to remove depleted fluid either pursuant to a preprogrammed profile or systematically, e.g., depleted fluid is brought into contact every 20 minutes with desiccant, by using a small lever or arm, or otherwise made to come into direct contact with the depleted carrier solution, resulting in absorption of the depleted carrier solution. Alternatively, a waste reservoir, e.g., a sponge, is lowered by a small lever or arm or otherwise to come into direct contact with the depleted carrier solution, resulting in immediate absorption of the depleted carrier solution. In a different embodiment a selectively permeable membrane surrounds a sponge or absorbent material, and the selectively permeable membrane primarily allows the solvent to pass through it (whether due to electric charge of the molecule or molecular size or acidity of the solvent vs. the drug or some other regulating means) and this semi permeable membrane either remains in constant contact with the diffusion surface or is periodically brought in to contact with the diffusion surface using an above described method. In a further embodiment a sponge or an absorbent material is in contact with the diffusion surface and a pre-tested and timed capillary action of the sponge is such that depleted carrier solution is absorbed at the right time and in proper amounts as to assist with the achievement of preprogrammed dosage profiles, i.e., even though much active substance may be absorbed along with the carrier solution still sufficient drug is present to achieve the objectives.

Modulated dispensing of drug formula brings about a significant increase of delivery rate over the one-time addition of formula at equal drug concentration. Thus, maximization of drug delivery rate is achieved. This is because the removal of solvent from the relatively small dispensed volume creates in situ an increase of drug concentration with subsequent saturation and precipitation of drug in the interface in immediate contact with the skin as evidenced by dryness of the interface. By the herein described method it is possible that the delivery rate of the active substance can be adjusted using the same drug solution by changing the dispensed volume of solution. Depending on the field of application it was found that about 2 gram of desiccant are sufficient for trapping solvent over at least 9 hours when e.g., dispensing 40 μl/hr of a given drug formula. It was found that increase of drug concentration in the formula causes a corresponding increase of delivery rate for dispensing of e.g., 40 μl/hr but not for e.g., 15 μl/hr. Apparently, dryness of the interface for the latter dispensing volume is achieved far before each consecutive dispensing step, thus hampering drug permeation.

Depending on the field of application, solvent removal means may be for example: a desiccant in a bag, any other absorbent material in a bag, a desiccant/absorbent connected to the interface by a tube, a desiccant/absorbent connected to the interface by a tube which comprises a valve, a compartment connected to the environment for evaporation, a compartment through which gas is guided to promote evaporation, an absorbent sponge, an absorbent sponge attached to an arm that moves it to and away from the interface, an absorbent sponge with a gas blowing device for drying. The material surrounding the solvent removal means preferably is made out of tissue, cloth, membrane, etc. The administration device (compartment) may comprise, if appropriate, at least one sensor, e.g., a humidity sensor for feedback control to the dispenser.

The solvent recovery means serves to remove depleted solvent from the active area of the administration reservoir such that the active substance concentration is maintained at a certain concentration and no unwanted substance is accumulated within the administration device. Upon quitting dispensing of formula into the administration device, the residual solvent is recovered and dryness of the interface is achieved, which results in controlled termination of drug delivery into skin. Normally the temperature of skin is sufficient to evaporate and discharge the solvent. However, a heating element or other helping means may be used for supporting evaporation.

The solvent recovery means are normally arranged at a certain distance from the interface, the administration reservoir respectively, is preventing uncontrolled absorption of solvent. The separation layer may e.g., comprise or consist of an inert foam or an appropriate cellular material or honeycomb. The solvent recovery means are preferably located within the administrative device and preferably comprise one or more desiccants and/or general or selective adsorbents such as silica gel, molecular sieves or active carbon preferably surrounded by a non-wettable material permeable for the vapors of solvent, e.g., such as Gore-Tex®.

Subsequent the method will be described in a general manner: The drug formulation is dispensed into the administration reservoir by the dispensing system. The volume and frequency of dispensing are freely programmable and are used to control the delivery rate and the time pattern of delivery of the chemical substance into the skin. The chemical substance is delivered from the administration reservoir by diffusion in the skin or onto the surface of the skin. The solvent recovery element reclaims solvent that was dispensed with the formulation into the administration reservoir. The solvent recovery element is in close vicinity to but in general not in direct contact with the administration reservoir to avoid uncontrolled absorption of solvent.

The volatile solvent evaporates from the interface under the influence of body heat and the vapors are trapped by the solvent recovery means, e.g., a chamber filled with absorbing material. The solvent recovery element serves the purpose of removing depleted solvent from the patch reservoir so that, after repeated dispensing, drug concentration maintains its highest value and no detrimental fluid (liquid) is accumulated within the administrating device. Upon quitting dispensing of drug formula, the residual solvent is recovered and dryness of the interface is achieved, which brings about stoppage of drug delivery.

Applications—ArisePatch™

A contemplated consumer product is the ArisePatch™. Most people experience difficulty and discomfort when waking early in the morning. According to a 2002 National Sleep Foundation poll 49% of US adults age 18-29 have trouble waking in the morning and 41% of US adults age 30-64 have trouble waking in the morning. There are 165, 000,000 adults in the US alone age 18-64, meaning approximately 74, 250,000 US adults age 18-64 have trouble waking in the morning.

Figure 5:
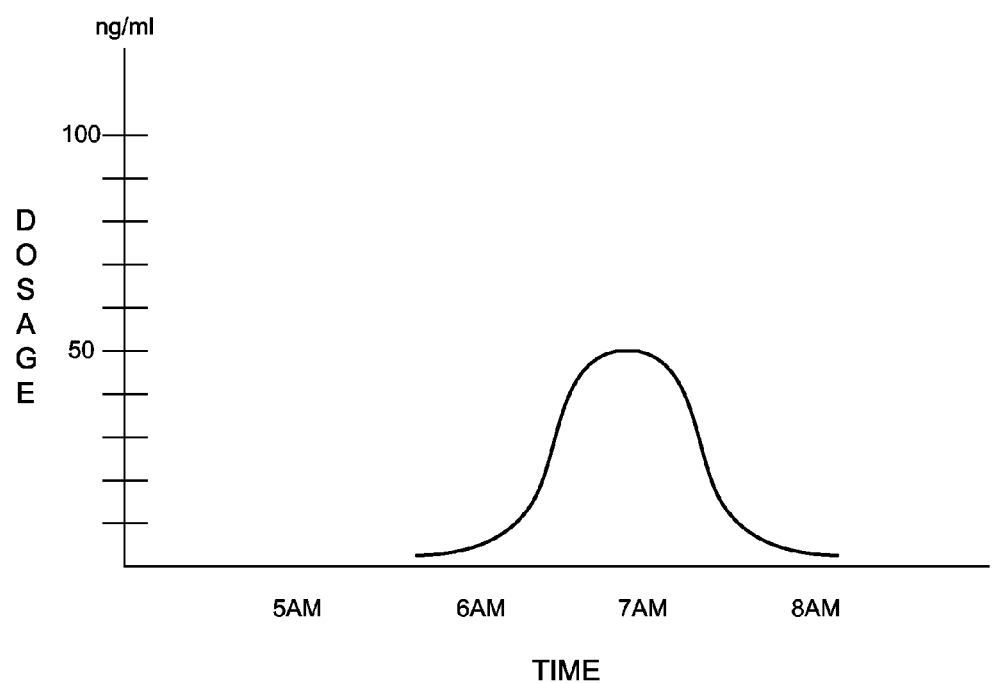
FIG. 5 shows an exemplary administration profile for a stimulant delivery system.

The ArisePatch implementation of the present invention allows individuals, while asleep, to have an over-the-counter (OTC) or prescription stimulant automatically administered during a 1-2 hour pre-wake-up period. FIG. 5 illustrates an exemplary stimulant administration profile showing a blood plasma level of ephedrine in nanograms per milliliter on the vertical axis, with time on the horizontal axis. Stimulant concentrations will reach peak levels immediately prior to having to wake. Immediately upon waking up the individual will be alert and feel well rested. The ArisePatch™ will eliminate the typical discomfort or difficulty associated with getting up early. This functionality is attractive to employed people getting up for work to ensure punctuality, and just about anyone who wants to offset morning discomfort associated with a late night, jet lag, or sickness.

Applications—Smoking Cessation

Nicotine replacement has been the most frequently used therapy to support smokers in their effort to quit. Smokers report that the craving for a cigarette is greatest immediately upon waking in the morning. The time elapsed between wakening and the first cigarette is the best indicator of addiction. For most smokers this time only a few minutes.

Current nicotine patches cause severe sleep disturbances by releasing nicotine steadily throughout the night to ensure sufficient morning nicotine levels to offset the strong morning craving. It is widely accepted that current nicotine patches have a detrimental and common side effect-sleeping disorders, and insomnia, including persistent nightmares. Therefore, users are often forced to remove the patch in the evening before they go to bed. This eliminates sleep disturbances, but results in nicotine levels that are insufficient to offset the strong morning craving. This is a major drawback to current nicotine patches and many users relapse, resulting in a less efficient smoking cessation therapy. Current patches present the user with a difficult decision, choosing between nightmares and relief from the strong morning cravings.

An exemplary product contemplated by the present invention is called Nicotine ChronoDose™ system. In accordance with the present invention, the system can begin to administer nicotine (or nicotine analogs or any other smoking cessation compound including but not limited to Zyban) automatically during a one hour period immediately prior to waking. This will relieve the smoker's peak craving upon waking without causing nightmares and insomnia. We believe that this system clearly provides a superior method for smoking cessation.

Figure 6:
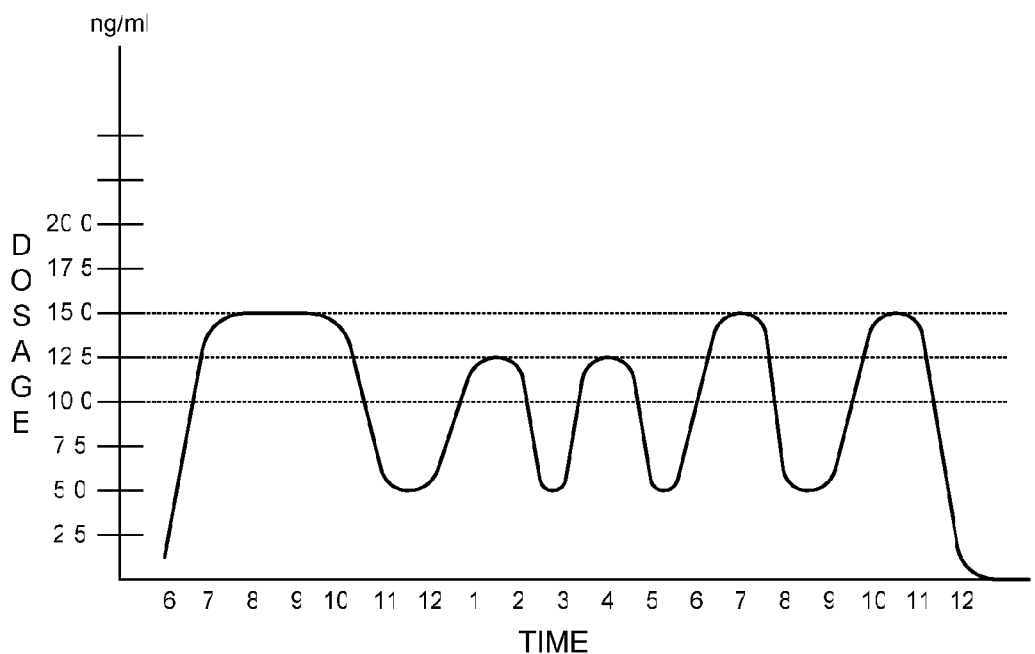
FIG. 6 shows an exemplary administration profile for a nicotine delivery system.

A more advanced nicotine replacement system than that described above is worn for three days at a time and is programmed to release nicotine in a daily rhythmic pattern such as shown in FIG. 6 to offset peaks in a smoker's cravings. FIG. 6 illustrates an exemplary nicotine administration profile showing a blood plasma level of nicotine in nanograms per milliliter on the vertical axis, with time on the horizontal axis. This implementation will reduce nicotine dependency by administering pre-programmed levels of nicotine pursuant to typical smoking patterns. For instance many smokers report that cravings for a cigarette are greatest upon waking up, after lunch, midafternoon, after dinner and before bedtime. This implementation of the present invention will automatically release larger doses of nicotine to offset peak cravings and no nicotine when cravings are typically at a minimum. The present invention may be delivered in a preprogrammed manner for each treatment regimen. The only involvement by the user will be the replacement of the 'reservoir' every three days, and the replacement of the platform housing as needed.

This implementation represents a tremendous move forward in nicotine replacement therapy, and is far superior to the old-technology systems that simply release the same amount of nicotine all day and night. With the present invention, one can systematically decrease a smoker's tolerance without increasing dependence (the result of a constant flow) and better wean a smoker off nicotine. This will allow the smoker to better 'tailor-down' and decrease the amount of nicotine he needs to quit. Modern smoking cessation is much more than nicotine replacement therapy. Programs also include weight control, diet and psychological support. The present invention fits well into these programs, since it addresses the key component of being able to quit smoking by efficiently countering the withdrawal symptoms while doing away with the negative side effects of current nicotine replacement therapy systems, namely sleep disturbance.

Applications—Cold and Flu Treatment

Cold and flu symptoms are worst from midnight until the early morning because the concentration of cortisol is lowest at that time. Current night time cold and flu medication end up losing efficacy by early morning when cold and flu symptoms are highest. Therefore people suffering from a cold or flu are often unpleasantly awoken by an increase in symptoms, cutting sleep short. Set and put on before bedtime, the present invention will automatically deliver a larger dose of medication and immuno-boosters in the early morning hours to more effectively combat the peak cold and flu symptoms that occur in the morning. Users will experience less severe cold and flu symptoms during the morning hours, will not have their sleep cycle cut short, and will wake up feeling symptom-free. This implementation uses prescription or OTC cold medicine alone or optionally in combination with certain transdermally efficacious vitamins and immune system boosters to provide a total solution to cold and flu ailments. This is the first cold therapy that combines OTC medicine with supplemental immuno-boosters in a comprehensive and automated manner. Our system will treat the cold symptoms directly and boost the body's immune system to help it heal naturally.

In a particular application, the Cold and Flu automated transdermal drug delivery system utilizes OTC cold medicine, Vitamin C, *Echinacea*, and Zinc to provide a total solution to cold and flu ailments, and all while you sleep. Cold and flu symptoms are worst in the middle of the night and early morning because the hormone cortisol, a key inflammation fighter, is missing at that time. Cold and flu symptoms are worst from midnight until the early morning because the concentration of cortisol is lowest at that time. Current night time cold and flu medication end up losing efficacy by early morning when cold and flu symptoms are highest. Therefore people suffering from a cold or flu are often unpleasantly awoken by an increase in symptoms, cutting sleep short.

Set and put on before bedtime, the Cold and Flu automated transdermal drug delivery system utilizes our proprietary technology to automatically deliver a larger dose of medication and immuno-boosters in the early morning hours to more effectively combat the peak cold and flu symptoms that occur in the morning. Users will experience less severe cold and flu symptoms during the morning hours, will not have their sleep cycle cut short, and will wake up feeling symptom-free.

Our system not only combats statistically proven peak nighttime and early morning cold symptoms by releasing OTC cold medicine, but actually helps your body to heal by boosting its immune system through Vitamin C, *Echinacea* and Zinc supplementation in small but distinct doses all night long.

Our Cold/Flu system releases these combination of compounds every 2 hours throughout the night, with a higher dosage of compounds being released in the morning to combat these proven middle of the night and early morning symptoms, which are the worst of the day.

Cold and flu symptoms are worst in the middle of the night and early morning because the hormone cortisol, a key inflammation fighter, is missing at that time. Our system utilizes its core competitive advantage by preprogramming our System to release more medicaments precisely at that time to offset these peak symptoms. Current cold and flu medications end up losing efficacy by early morning when cold symptoms peak, so the user either has sleep cut short due to the onset of these symptoms, or wakes up out of slumber feeling sick with peak symptoms. Our system will ensure that a while a person is actually sleeping, a sufficient dose of cold and flu medicine is freshly delivered to offset these peak morning symptoms.

Applications—Weight Control, Vitamin and Herbal Supplementation

In yet another application, a series of weight loss vitamins and supplements is administered in small distinct doses many times over a multiple day period. Vitamins and supplements are absorbed by the body in small dosages. Contrary to popular belief, once-a-day products are not maximally effective because excess dosages are excreted unused. This implementation of the present invention precisely controls the timing and dosage of small but distinct amounts of vitamins and supplements during a 24 hour period to ensure that vitamins and supplements are constantly bio-available for optimal absorption and cellular function. Greater doses are automatically released prior to mealtimes to counter appetite cravings, resulting in a much more effective diet program.

Applications—Angina

Research shows that variant angina occurs 30 times more often between 2:00 a.m. and 4:00 a.m. ('critical angina phase') than at any other time of the day. Nitroglycerin effectively combats angina attacks, if administered in optimal doses. Current nitroglycerin patches exist, but they can only release a constant amount of nitroglycerine steadily over time. Current patches cannot tailor the release of nitroglycerine to optimize treatment by releasing more nitroglycerine precisely during the critical angina phase to offset these peak symptoms.

In addition, nitroglycerine loses its effectiveness and requires higher and higher dosages when administered constantly. Our bodies become tolerant to it. Current systems cannot stop or decrease the release of nitroglycerine when disease symptoms are lowest. Thus, these current 'dumb' patches cannot offset the critical angina phase by releasing more of the drug, nor can they shut down or stop nitroglycerine administration when the body doesn't need it. It is a 'one dose fits all' type of scenario once each "dumb" patch is applied to the patient.

The method in accordance with the present invention utilizes an automated transdermal system in order to transdermally administer more nitroglycerine during the critical angina phase to ensure adequate offset of these symptoms and less nitroglycerine when it is not needed so that no tolerance builds up. Our method utilizes a 'smart' patch medicine system at this time to offset these peak critical phases in the disease cycle arising due to the human body's circadian rhythm.

The preprogrammable automated transdermal system is worn around the wrist like a watch (or the forearm arm or ankle) and releases nitroglycerine in optimal dosages at times that are optimally synchronized. This is pursuant to a preprogrammed and tailored dosage profile. Current nitroglycerin patches only have the capability to release a constant dose of nitroglycerin over a period of time. Current nitroglycerin patches simply cannot alter or vary dosages to increase dosages at different times of the day, and decrease dosages at other times of the day.

The nitroglycerin system in accordance with the present invention has three primary advantages over current nitroglycerin patches. First, the system utilizes its core competitive advantage to automatically and precisely release nitroglycerin in peak amounts to offset the peak symptoms of morning attacks occurring during the critical angina phase. Current nitroglycerine patches have release rates that stay constant and do not increase to offset critical phases, and do not decrease as symptoms decrease. Second, our system solves the tolerance issue by releasing less (or no) nitroglycerin in off-peak hours, and then releasing nitroglycerin at just the right time so that it is present during critical periods, without increasing tolerance. Third, our system accomplishes 1 and 2 above automatically, without the need for a patient to wake up to take a drug at this critical phase, which does away with the need for any increased patient compliance.

As a result we believe that our nitroglycerin system represents an ideal delivery system for patients who use nitroglycerin regularly for the treatment and/or the prevention of heart attacks and strokes. Patient compliance regarding the timing and dose of heart attack medication is crucial. Patient non-compliance with physician's instructions for this is often a cause of re-hospitalization, according to the US Department of Health and Human Services. The system solves this problem, and will decrease the need for re-hospitalization by dramatically increasing patient compliance.

This system can be either an 'wear each night and remove in the morning' system, whereby it only releases nitroglycerine automatically to offset the critical angina phase in the morning, or a 'total solution' system, that is worn for a period of 24 hours to several days, and that administers nitroglycerine in tailored amounts and at tailored times as synchronized with the body's circadian rhythm (and conveniently taken off while showering or swimming).

The system is an innovative new drug therapy for angina. With its superior advantage of optimized and automated time and dose administration synchronized with our circadian rhythms, the system in accordance with the present invention ensures that nitroglycerin will circulate in the bloodstream exactly when the patient needs it, and without any build up tolerance. For these reasons, our system is superior to current steady release nicotine patches. Our system's increased advantages are extremely relevant for those patients with moderate to severe angina.

Figure 7:
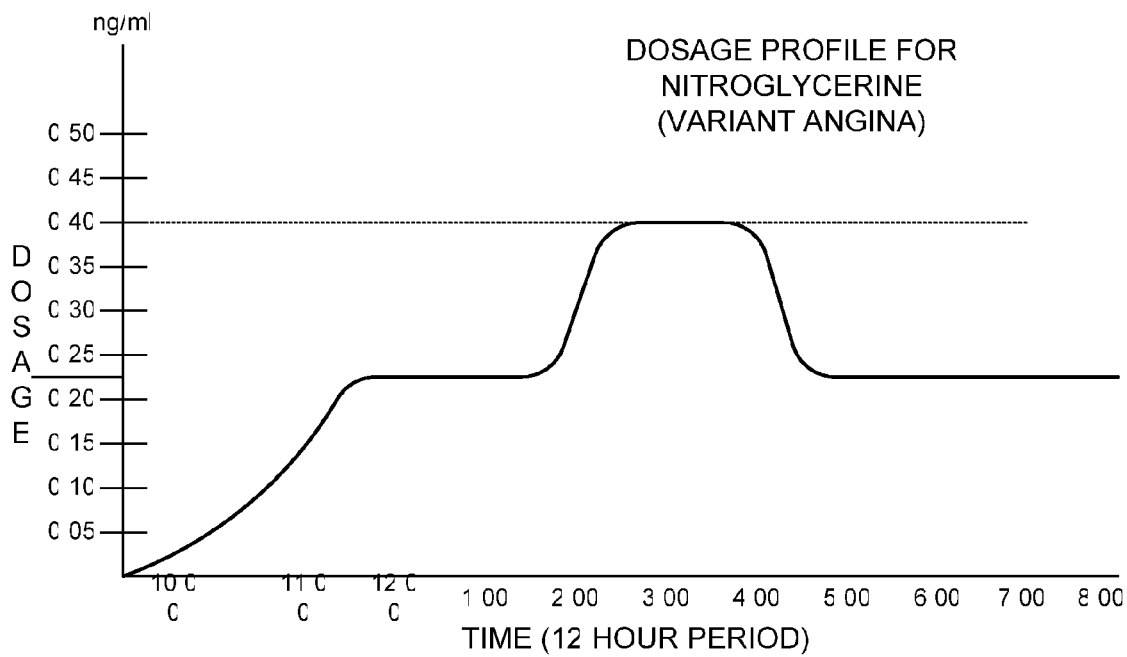
FIG. 7 shows an exemplary administration profile for a nitroglycerine delivery system tailored to treat variant angina attacks.

FIG. 7 shows an exemplary administration profile for a nitroglycerine delivery system tailored to treat variant angina attacks or angina pectoris. This type of angina attack has a peak frequency in many patients between the hours of 2:00 and 4:00 A.M. This is a particularly difficult time to wake up to take a drug such as nitroglycerine. In accordance with the present invention an administration profile substantially like that shown in FIG. 7 is automatically administered. In FIG. 7 the vertical axis indicates blood plasma level in nanograms per milliliter, and the horizontal axis indicates time from 10:00 P.M. through the night to 8:00 A.M.

Figure 8:
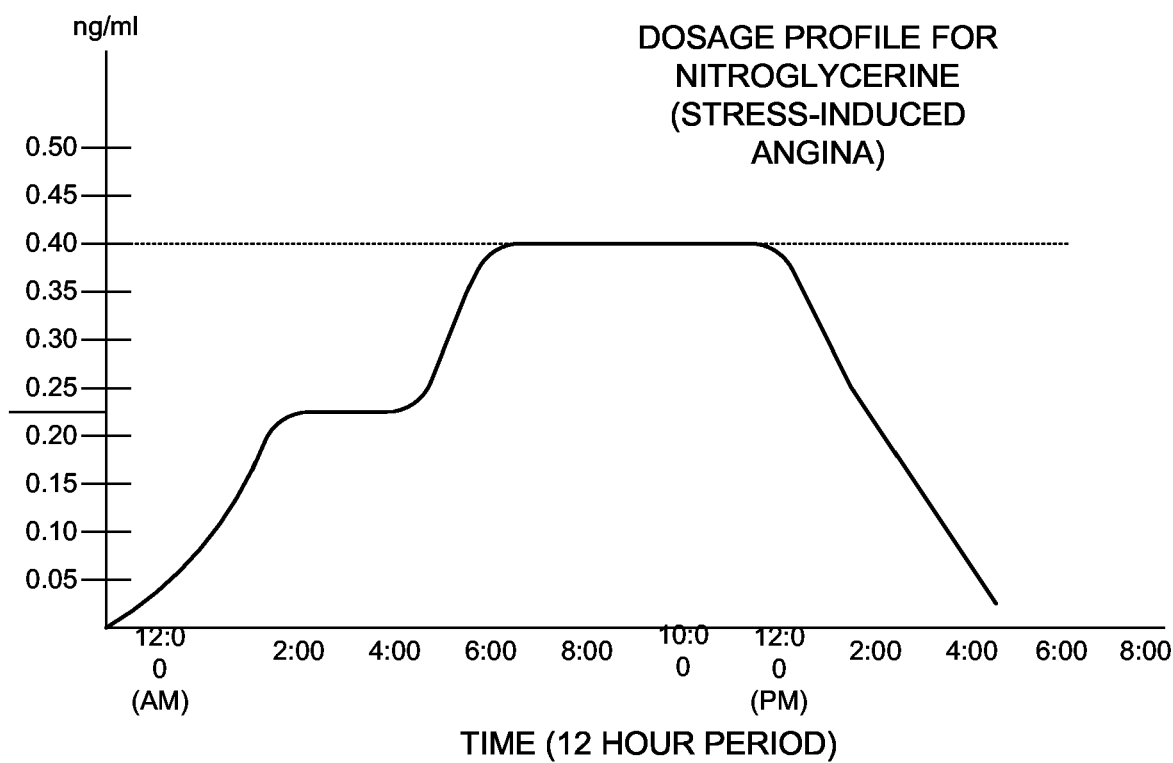
FIG. 8 illustrates an exemplary administration profile for a nitroglycerine delivery system tailored to treat stress-induced angina attack.

FIG. 8 illustrates an exemplary administration profile for a nitroglycerine delivery system tailored to treat stress-induced angina attack. In FIG. 8 the vertical axis indicates blood plasma level in nanograms per milliliter, and the horizontal axis indicates time from 12:00 A.M. through the day until about 4:00 P.M. The administration profile shown in FIG. 8 provides a high blood plasma concentration throughout the waking hours of a day when stress is likely occur.

Applications—Asthma

The automated transdermal asthma system automatically administers a morning dose of albuterol, tolobuterol, salmeterol, beta 2 agonist or any other antiarrhythmic drug (an 'Asthma drug') to combat the peak symptom of morning asthma attacks known as the 'morning dip'.

Asthma attacks occur 100 (one hundred) times more often between the hours 4 A.M. and 6 A.M., when most people are asleep. This is due to the early morning deterioration of respiratory function known as 'morning dip', which is the time of day that respiratory function is at its lowest. These early morning asthma attacks cause great distress to sufferers and care providers. The morning dip represents the dip in respiratory function at this time when asthma attacks are 100 times more likely to occur. Our system effectively combats the morning dip by releasing more Asthma drug at this time to offset this peak morning symptom. In other words, our 'smart' patch varies the level of drug in the bloodstream so that drug concentrations are highest when respiratory function is at its lowest.

Current 'dumb' asthma patches exist, but they can only release a constant amount of drug steadily over time. Current patches cannot tailor the release of drug to optimize treatment by releasing more drug precisely during the morning dip to offset these peak critical symptoms.

The Asthma system has two primary advantages over current patches. First, the system of the present invention utilizes its core competitive advantage to automatically and precisely release albuterol or other asthma drugs in peak amounts to offset the peak symptoms associated with the morning dip. Current patches have release rates that stay constant and do not increase to offset this peak critical phases, and do not decrease as symptoms decrease. Second, our system accomplishes 1 and 2 above automatically, without the need for a patient to wake up to take a drug at this critical phase, which does away with the need for any increased patient compliance.

The automated transdermal system for Asthma is worn around the wrist like a watch (or the forearm arm or ankle) and releases albuterol or other Asthma drugs in optimal dosages at times that are optimally synchronized, especially to offset the morning dip, pursuant to a preprogrammed and tailored dosage profile. Current Asthma patches only have the capability to release a constant dose over a period of time. Current Asthma patches simply cannot alter or vary dosages to increase dosages at different times of the day, and decrease dosages at other times of the day.

The system is an innovative new drug therapy for asthma. With its superior advantage of optimized and automated time and dose administration synchronized with our circadian rhythms, our system ensures that albuterol or another asthma drug will circulate in increased amounts in the bloodstream exactly when the patient needs it. For these reasons, our system is superior to current steady release patches. Our system's increased advantages are extremely relevant for those patients with moderate to severe asthma.

Applications—Hypertension

The clondine automated transdermal system utilizes clondine, (or another hypertension drug) an effective drug that combats high blood pressure. The clondine automated transdermal drug delivery system has an automated morning release of clondine to combat the peak symptom of morning heart attacks.

Blood pressure differs at different times of the day. Blood pressure surges upon waking, and is lower by 20 to 30 percent while sleeping. Our preprogrammed automatic transdermal system utilizes its core competitive advantage by releasing clondine in a tailored fashion to counter high blood pressure when symptoms are highest, while releasing less clondine when symptoms are less severe.

Current clondine patches release the drug consistently over time. It cannot release more of the drug when symptoms are worst. People die most when the symptoms peak. Having the advantage of administering more of the drug when a patient needs it the most can mean the difference between life and death, especially in patients with moderate to severe high blood pressure.

The automated transdermal system for hypertension has two primary advantages over current patches. First, our system utilizes its core competitive advantage to automatically and precisely release clondine or other hypertension drugs in peak amounts to offset the peak symptoms associated with the dangerous morning symptoms. Current hypertension patches have release rates that stay constant and do not increase to offset this peak critical phases, and do not decrease as symptoms decrease. Second, our system accomplishes 1 and 2 above automatically, without the need for a patient to wake up to take a drug at this critical phase, which does away with the need for any increased patient compliance.

Applications—Depression, Alzheimer's, Attention Deficit

The selegiline automated transdermal system utilizes selegiline, an effective MAO inhibitor for the treatment of depression, Alzheimer's and Attention Deficit Disorder.

The selegiline automated transdermal drug delivery system gives an automated morning release of selegiline to combat the peak symptom of morning depression without the side effect of sleep disturbances.

The system in accordance with the present invention is applied before bed. It does not release the drug until an hour or 2 before morning, so symptom of morning depression would be corrected by our system without subjecting the patient to sleep disturbances.

Primary negative side effects of the selegiline patches are abnormal dreams, insomnia, and difficulty sleeping. We believe that by specifically refraining from administering selegiline at night, and utilizing our system's core competitive advantage to turn it on an hour or so before waking, we can do away with this negative side effect and still offset the critical phase of morning symptoms of depression. It has been reported that patients have increased symptoms of depression upon waking if the critical amount of Selegiline is not circulating through their system. Our system utilizes its core competitive advantage to provide a compelling solution to this problem. Our system is applied before bed, it would not release the drug until an hour or two before morning, so symptom of morning depression would be corrected by our system without subjecting the patient to sleep disturbances.

Current Oral Selegiline produces horrible side effects. There is a new Selegiline patch coming out on the market, but it to produces sleep disturbances. It is believed that the system in accordance with the present invention would be superior to conventional Selegiline product delivery systems.

Applications—In General

The present invention is particularly useful in applications in which it is necessary and/or desirable to start the administration of a drug, stop the administration of a drug, and/or increase/decrease the dosage of a drug at a time when it is inconvenient or impossible for a patient to initiate the necessary actions. This is particularly useful for a wide variety of drug administration applications that benefit when administration is started, stopped, or changed while a person is sleeping. As chronotherapy knowledge increases, it is contemplated that a wide variety of applications will be discovered in which benefit is realized by starting, stopping and/or changing the drug administration while a patient sleeps.

In each of the examples, treatment is continued as needed to provide superior symptomatic relief, prevent exacerbation of symptoms, and/or prevent and/or delay progression of the disease state or condition in the patient, or until it is no longer well tolerated by the patient, or until a physician terminates treatment. For example, a physician may monitor one or more symptoms and/or serum levels of active material and/or metabolic by-product(s) in a patient being treated according to this invention and, upon observing attenuation of one or more symptoms for a period of time, conclude that the patient can sustain the positive effects of the above-described treatment without further administration for a period of time. When necessary, the patient may then return at a later point in time for additional treatment as needed.

As used herein, 'day' means a 24-hour period. Thus, for example, 'for at least three consecutive days' means for at least a 72-hour period. During or after the treatment, a physician may monitor one or more symptoms and/or serum levels in the patient and, upon observing an improvement in one or more of the parameters for a period of time, conclude that the patient can sustain the positive effects of the treatment without further administration of the active material for a period of time.

In order to use an active material for therapeutic treatment (including prophylactic treatment) of mammals including humans according to the methods of this invention, the active material is normally formulated in accordance with standard pharmaceutical practice as a pharmaceutical composition. According to this aspect of the invention there is provided a pharmaceutical composition comprising an active material in association with a pharmaceutically acceptable diluting substance or carrier, wherein the active material is present in an amount for effective treating or preventing a particular condition. While individual needs may vary, determination of optimal ranges for effective amounts of an active ingredient (alone or in combination with other drugs) within the ranges disclosed herein is within the expertise of those skilled in the art. Accordingly, 'effective amounts' of each component for purposes herein are determined by such considerations and are amounts that improve one or more active ingredient functions and/or ameliorate on or more deleterious conditions in patients and/or improve the quality of life in patients.

The present invention also provides pharmaceutical kits for treating a particular symptom, condition and/or disease and/or improving a particular biological function, comprising one or more containers comprising one or more active compositions in accordance with this invention. Such kits can also include additional drugs or therapeutics for co-use with the active composition for treatment or prevention of a particular symptom, condition and/or disease and/or improving a particular biological function. In this embodiment, the active composition and the drug can be formulated in admixture in one container, or can be contained in separate containers for simultaneous or separate administration. The kit can further comprise a device(s) for administering the compounds and/or compositions, such as device 100 shown in FIG. 1, and written instructions in a form prescribed by a governmental agency regulating the manufacture, use or sale of pharmaceuticals or biological products, which instructions can also reflect approval by the agency of manufacture, use or sale for human administration.

Although the invention has been described and illustrated with a certain degree of particularity, it is understood that the present disclosure has been made only by way of example, and that numerous changes in the dosages, administration profiles, timing, as well as the combination and arrangement of parts can be resorted to by those skilled in the art without departing from the spirit and scope of the invention, as hereinafter claimed.

What is claimed is:

1. A method for delivering an active substance to a user, the method comprising:
   placing a skin interface of a delivery device in contact with the user's skin, the delivery device comprising a reservoir containing the active substance and a solvent, a programmable dosage controller configured to control the time and dosage of the active substance from the reservoir to the skin interface according to a dosage profile corresponding to a circadian rhythm of the user;
   dispensing a portion of the active substance and the solvent from the reservoir to the skin interface according to the dosage profile;
   delivering the active substance through the skin interface to the user's skin; and
   removing a residual portion of the solvent from the skin interface using a solvent removal element in the delivery device positioned in a spaced apart relation to the skin interface after completing the dispensing a portion of the active substance delivery according to the dosage profile.

2. The method of claim 1, wherein the skin interface comprises a permeable membrane.

3. The method of claim 2, wherein delivering the active substance through the skin interface includes delivering the active substance across a surface area of the permeable membrane to the skin.

4. The method of claim 1, wherein the programmable dosage controller is configured to control a valve in fluid communication with the reservoir.

5. The method of claim 1, wherein the delivery device is adhesively attached to the skin.

6. The method of claim 1, wherein the programmable dosage controller comprises timing routines corresponding to the circadian rhythm.

7. The method of claim 6, wherein the timing routines are selected to deliver the active substance at a time, rate, sequence and/or cycle corresponding to the circadian rhythm.

8. The method of claim 1, wherein the active substance comprises nicotine and the dosage profile is configured to deliver the nicotine at times that are associated with nicotine cravings.

9. The method of claim 8, wherein at least one of the times corresponds to a time at which the user experiences a morning nicotine craving.

10. The method of claim 1, further comprising: removing the delivery device after contacting the skin for greater than 24 hours.

11. The method of claim 1, further comprising: removing the delivery device after contacting the skin for greater than 72 hours.

12. The method of claim 1, further comprising: replacing the reservoir with a second reservoir containing an active substance and a solvent.

13. The method of claim 12, further comprising: using the delivery device with the second reservoir for greater than 72 hours.

14. The method of claim 1, wherein the active substance comprises a stimulant and the dosage profile is configured to deliver the stimulant during a 1-2 hour pre-wake-up period.

15. The method of claim 1, wherein the active substance comprises cold medicine and the dosage profile is configured to deliver the cold medicine while the user sleeps.

16. The method of claim 15, further comprising dispensing vitamins and/or minerals to the skin interface while the user sleeps.

17. The method of claim 1, wherein the active substance comprises nitroglycerine and the dosage profile is configured to deliver the nitroglycerine while the user sleeps in first amount in a first time period and in a second amount higher than the first amount in a second time period.

18. The method of claim 1, wherein the active substance is an asthma drug and the dosage profile is configured to deliver the asthma drug while the user sleeps.

19. The method of claim 1, wherein the active substance is a hypertension drug and the dosage profile is configured to deliver the hypertension drug while the user sleeps.

20. The method of claim 1, wherein the active substance is selegiline and the dosage profile is configured to deliver the selegiline while the user sleeps.

* * * * *